(12) United States Patent
Duke et al.

(10) Patent No.: US 8,532,933 B2
(45) Date of Patent: Sep. 10, 2013

(54) INSULIN OPTIMIZATION SYSTEMS AND TESTING METHODS WITH ADJUSTED EXIT CRITERION ACCOUNTING FOR SYSTEM NOISE ASSOCIATED WITH BIOMARKERS

(75) Inventors: David L. Duke, Fishers, IN (US); Matthew W Percival, Mountain View, CA (US); Abhishek Soni, Indianapolis, IN (US); Steven Bousamra, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 227 days.

(21) Appl. No.: 12/818,795

(22) Filed: Jun. 18, 2010

(65) Prior Publication Data

US 2011/0313674 A1    Dec. 22, 2011

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................... 702/19; 702/22; 703/11; 703/12

(58) Field of Classification Search
None
See application file for complete search history.

(56) References Cited

U.S. PATENT DOCUMENTS

| | | | |
|---|---|---|---|
| 4,151,845 A | 5/1979 | Clemens | |
| 4,731,726 A | 3/1988 | Allen, III | |
| 4,803,625 A | 2/1989 | Fu et al. | |
| 5,364,346 A | 11/1994 | Schrezenmeir | |
| 5,377,258 A | 12/1994 | Bro | |
| 5,572,421 A | 11/1996 | Altman et al. | |
| 5,576,952 A | 11/1996 | Stutman et al. | |
| 5,665,065 A | 9/1997 | Colman et al. | |
| 5,722,418 A | 3/1998 | Bro | |
| 5,822,715 A | 10/1998 | Worthington et al. | |
| 5,840,020 A | 11/1998 | Heinonen et al. | |
| 5,868,669 A | 2/1999 | Iliff | |

(Continued)

FOREIGN PATENT DOCUMENTS

| | | | |
|---|---|---|---|
| DE | 102005041627 A1 | 3/2007 | |
| EP | 1 702 559 A2 | 9/2006 | |

(Continued)

OTHER PUBLICATIONS

Breton et al. (Journal of Diabetes Science and Technology, 2008, 2(5), 853-862).*

(Continued)

*Primary Examiner* — Larry D Riggs, II
(74) *Attorney, Agent, or Firm* — Dinsmore & Shohl LLP

(57) ABSTRACT

Embodiments of a testing method for optimizing a therapy to a diabetic patient comprise collecting at least one sampling set of biomarker data, computing a probability distribution function, a hazard function, a risk function, and a risk value for the sampling set of biomarker data wherein, wherein the probability distribution function is calculated to approximate the probability distribution of the biomarker data, the hazard function is a function which yields higher hazard values for biomarker readings in the sampling set indicative of higher risk of complications, the risk function is the product of the probability distribution function and the hazard function, and the risk value is calculated by the integral of the risk function, minimizing the risk value by adjusting the diabetic patient's therapy, and exiting the testing method when the risk value for at least one sampling set is minimized to an optimal risk level.

61 Claims, 12 Drawing Sheets

(56) References Cited

U.S. PATENT DOCUMENTS

| | | |
|---|---|---|
| 5,879,163 A | 3/1999 | Brown et al. |
| 5,897,493 A | 4/1999 | Brown |
| 5,971,922 A | 10/1999 | Arita et al. |
| 6,018,713 A | 1/2000 | Coli et al. |
| 6,108,665 A | 8/2000 | Bair et al. |
| 6,234,964 B1 | 5/2001 | Iliff |
| 6,241,633 B1 | 6/2001 | Conroy |
| 6,326,160 B1 | 12/2001 | Dunn et al. |
| 6,338,039 B1 | 1/2002 | Lonski et al. |
| 6,352,505 B1 | 3/2002 | Bortz |
| 6,379,301 B1 | 4/2002 | Worthington et al. |
| 6,424,847 B1 | 7/2002 | Mastrototaro et al. |
| 6,425,863 B1 | 7/2002 | Werner et al. |
| 6,544,212 B2 | 4/2003 | Galley et al. |
| 6,567,785 B2 | 5/2003 | Clendenon |
| 6,645,368 B1 | 11/2003 | Beaty et al. |
| 6,656,114 B1 | 12/2003 | Poulsen et al. |
| 6,691,043 B2 | 2/2004 | Ribeiro, Jr. |
| 6,770,029 B2 | 8/2004 | Iliff |
| 6,835,175 B1 | 12/2004 | Porumbescu |
| 6,923,763 B1 | 8/2005 | Kovatchev et al. |
| 6,954,662 B2 | 10/2005 | Freger et al. |
| 7,229,430 B2 | 6/2007 | Hickle et al. |
| 7,241,265 B2 | 7/2007 | Cummings et al. |
| 7,266,400 B2 | 9/2007 | Fine et al. |
| 7,278,983 B2 | 10/2007 | Ireland et al. |
| 7,381,523 B2 | 6/2008 | Efendic |
| 7,389,133 B1 | 6/2008 | Kotulla et al. |
| 7,404,796 B2 * | 7/2008 | Ginsberg ............... 600/365 |
| 7,405,196 B2 | 7/2008 | Rosskamp et al. |
| 7,413,749 B2 | 8/2008 | Wright et al. |
| 7,509,156 B2 | 3/2009 | Flanders |
| 7,553,281 B2 | 6/2009 | Hellwig et al. |
| 7,676,329 B2 | 3/2010 | Garczarek et al. |
| 7,685,000 B1 | 3/2010 | Petit et al. |
| 7,734,323 B2 | 6/2010 | Blomquist et al. |
| 7,761,310 B2 | 7/2010 | Rodgers |
| 7,766,830 B2 | 8/2010 | Fox et al. |
| 8,078,592 B2 | 12/2011 | Gejdos et al. |
| 8,117,020 B2 | 2/2012 | Abensour et al. |
| 2002/0107476 A1 | 8/2002 | Mann et al. |
| 2002/0161288 A1 | 10/2002 | Shin et al. |
| 2003/0028399 A1 | 2/2003 | Davis et al. |
| 2003/0104982 A1 | 6/2003 | Wittmann et al. |
| 2003/0130616 A1 | 7/2003 | Steil et al. |
| 2003/0208113 A1 | 11/2003 | Mault et al. |
| 2003/0211617 A1 | 11/2003 | Jones |
| 2004/0122701 A1 | 6/2004 | Dahlin et al. |
| 2004/0122709 A1 | 6/2004 | Avinash et al. |
| 2004/0247748 A1 | 12/2004 | Bronkema |
| 2005/0020903 A1 | 1/2005 | Krishnan et al. |
| 2005/0021372 A1 | 1/2005 | Mikkelsen et al. |
| 2005/0049179 A1 * | 3/2005 | Davidson et al. ............ 514/3 |
| 2005/0119540 A1 | 6/2005 | Potts et al. |
| 2006/0010098 A1 | 1/2006 | Goodnow et al. |
| 2006/0025931 A1 | 2/2006 | Rosen et al. |
| 2006/0030890 A1 | 2/2006 | Cosentino et al. |
| 2006/0031094 A1 | 2/2006 | Cohen et al. |
| 2006/0171503 A1 | 8/2006 | O'Hara et al. |
| 2006/0173406 A1 | 8/2006 | Hayes et al. |
| 2006/0195022 A1 | 8/2006 | Trepagnier et al. |
| 2006/0195342 A1 | 8/2006 | Khan et al. |
| 2006/0253296 A1 | 11/2006 | Liisberg et al. |
| 2006/0271404 A1 | 11/2006 | Brown |
| 2006/0287883 A1 | 12/2006 | Turgiss et al. |
| 2007/0048691 A1 | 3/2007 | Brown |
| 2007/0055483 A1 | 3/2007 | Lee et al. |
| 2007/0100659 A1 | 5/2007 | Preiss |
| 2007/0106135 A1 | 5/2007 | Sloan et al. |
| 2007/0198296 A1 | 8/2007 | Pellinat et al. |
| 2007/0213604 A1 | 9/2007 | Brown |
| 2007/0253904 A1 | 11/2007 | Gunton et al. |
| 2007/0282636 A1 | 12/2007 | Sauk et al. |
| 2008/0025591 A1 | 1/2008 | Bhanot et al. |
| 2008/0125636 A1 | 5/2008 | Ward et al. |
| 2008/0146895 A1 | 6/2008 | Olson et al. |
| 2008/0154513 A1 * | 6/2008 | Kovatchev et al. ............ 702/19 |
| 2008/0172027 A1 | 7/2008 | Blomquist |
| 2008/0177149 A1 | 7/2008 | Weinert et al. |
| 2008/0177165 A1 | 7/2008 | Blomquist et al. |
| 2008/0183494 A1 | 7/2008 | Cuddihy et al. |
| 2008/0201325 A1 | 8/2008 | Doniger et al. |
| 2008/0206799 A1 | 8/2008 | Blomquist |
| 2008/0214919 A1 | 9/2008 | Harmon et al. |
| 2008/0228056 A1 | 9/2008 | Blomquist et al. |
| 2008/0234943 A1 | 9/2008 | Ray et al. |
| 2008/0234992 A1 | 9/2008 | Ray et al. |
| 2008/0243902 A1 | 10/2008 | Rong et al. |
| 2008/0255438 A1 | 10/2008 | Saidara et al. |
| 2008/0262745 A1 | 10/2008 | Polidori |
| 2008/0269585 A1 | 10/2008 | Ginsberg |
| 2008/0306353 A1 | 12/2008 | Douglas et al. |
| 2008/0319384 A1 | 12/2008 | Yodfat et al. |
| 2009/0006061 A1 | 1/2009 | Thukral et al. |
| 2009/0018406 A1 | 1/2009 | Yodfat et al. |
| 2009/0150177 A1 | 6/2009 | Buck et al. |
| 2009/0150186 A1 | 6/2009 | Cohen et al. |
| 2009/0164239 A1 | 6/2009 | Hayter et al. |
| 2009/0176692 A1 | 7/2009 | Habermann et al. |
| 2009/0234262 A1 | 9/2009 | Reid et al. |
| 2009/0247836 A1 | 10/2009 | Cole et al. |
| 2009/0253970 A1 | 10/2009 | Bashan et al. |
| 2009/0253973 A1 | 10/2009 | Bashan et al. |
| 2009/0281393 A1 | 11/2009 | Smith |
| 2010/0016700 A1 | 1/2010 | Sieh et al. |
| 2010/0138197 A1 | 6/2010 | Sher |
| 2010/0141656 A1 | 6/2010 | Krieftewirth |
| 2010/0160757 A1 | 6/2010 | Weinert et al. |
| 2010/0174553 A1 | 7/2010 | Kaufman et al. |
| 2010/0198520 A1 | 8/2010 | Breton et al. |
| 2010/0222765 A1 | 9/2010 | Blomquist et al. |
| 2010/0262434 A1 | 10/2010 | Shaya |
| 2010/0265073 A1 | 10/2010 | Harper |
| 2010/0274497 A1 | 10/2010 | Rush |
| 2010/0330598 A1 | 12/2010 | Thukral et al. |
| 2010/0331650 A1 | 12/2010 | Batman et al. |
| 2010/0331651 A1 | 12/2010 | Groll |
| 2011/0071365 A1 | 3/2011 | Lee et al. |
| 2012/0226117 A1 | 9/2012 | Lamego et al. |

FOREIGN PATENT DOCUMENTS

| | | |
|---|---|---|
| EP | 1 728 469 A2 | 12/2006 |
| EP | 1 956 508 A2 | 12/2007 |
| EP | 2006786 A1 | 12/2008 |
| FR | 2760962 A1 | 3/1997 |
| WO | 94/20916 | 9/1994 |
| WO | 9901836 | 1/1999 |
| WO | 0009007 | 2/2000 |
| WO | 0122343 A2 | 3/2001 |
| WO | 0133314 A2 | 5/2001 |
| WO | 01/52727 A1 | 7/2001 |
| WO | 03/002258 A1 | 1/2003 |
| WO | 03/046695 A2 | 6/2003 |
| WO | 03/082096 A1 | 10/2003 |
| WO | 2004/015539 A2 | 2/2004 |
| WO | 2004/084820 A2 | 10/2004 |
| WO | 2007/081853 A2 | 7/2007 |
| WO | 2007117719 A2 | 10/2007 |
| WO | 2007144419 A2 | 12/2007 |
| WO | 2009/146119 A2 | 12/2009 |
| WO | 2010/000266 A1 | 1/2010 |
| WO | 2010072387 A2 | 7/2010 |
| WO | 2010089304 A1 | 8/2010 |
| WO | 2010089307 A1 | 8/2010 |
| WO | 2010/097796 A1 | 9/2010 |

OTHER PUBLICATIONS

Huang Elbert S., "The key to preventing burnout: understanding the burden of diabetes treatment", DiabetesVoice, vol. 53, Issue 3, pp. 33-35, Dec. 2008.

Larimer, et al., "Relapse Prevention, an Overview of Marlatt's Cognitive-Behavioral Model", Alcohol Research & Health, vol. 23, No. 2, pp. 151-160, 1999.

Marlatt et al., "Clinical Guidelines for Implementing Relapse Prevention Therapy", Addictive Behaviors Research Center/University of Washington, pp. 1-49, Dec. 2002.

International Search Report and Written Opinion completed Oct. 5, 2011, pertaining to International Application No. PCT/EP2011/002924.

Non-Final Office Action pertaining to U.S. Appl. No. 12/818,875, dated Apr. 2, 2012.

Montani et al., "Integrating Case Based and Rule Based Reasoning in a Decision Support System: Evalation with Simulated Patients", AMIA, Inc., pp. 887-891, 1999.

Montani et al., "Managing diabetic patients through a Multi Modal Reasoning methodology", International Journal of Medical Informatics, vol. 58, Complete, pp. 243-256, Sep. 1, 2000.

Schmidt et al., "Case-based Reasoning for Medical Knowledge-based Systems", Institute for Medical Informatics and Biometry, University of Rostock Rembrandtstr. 16/17, D-18055 Rostock, Germany, 2000.

Denis Raccah, "Insulin therapy in patients with type 2 diabetes mellitus: Treatment to target fasting and postprandial blood glucose levels", Insulin 1:158-165, 2006.

Morgan et al., "Uncertainty a Guide to Dealing with Uncertainty in Quantitative Risk and Poly Analysis", Cambridge University Press, pp. 307-310, 1990.

Brand et al., "Updating uncertainty in an integrated risk assessment: Conceptual framework and methods", Risk Analysis 1995 US, vol. 15, No. 6, pp. 719-731, 1995.

Accu-Chek Spirit Pump User Guide, Sep. 2008, pp. 1-201.

Accu-Chek Smart Pix Device Reader User's Manual, Sep. 2008, pp. 1-92.

Accu-Chek Aviva Blood Glucose Meter Owner's Booklet, Sep. 2008, pp. 1-92.

Accu-Chek Spirit Insulin Pump System, Pocket Compass Software with Bolus Calculator User Guide, Oct. 2005, pp. 1-174.

De Groen, et al., Applying World Wide Web Technology to the Study of Patients with Rare Diseases, Annals of Internal Medicine, vol. 129, No. 2, Jul. 15, 1998, pp. 107-113, XP002587966, 1998.

Gerstein et al., "A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia Treatment) Study", Diabetic Medicine, vol. 23, pp. 736-742, 2006.

Hirsch et al., "A Real-World Approach to Insulin Therapy in Primary Care Practice", Practical Pointers, Clinical Diabetes, vol. 23, Nov. 2, 2005.

Nathan et al., Medical Management of Hyperglycemia in Type 2 Diabetes: A Consensus Algorithm for the Initiation and Adjustment of Therapy, Diabetes Care, vol. 31, No. 12: pp. 1-11, Dec. 2008.

Riddle et al., "The Treat-to_Target Trial, Ramdomized addition of glargine or human NPH insulin to oral therapy of type 2 diabetic patients" Diabetes Care, vol. 26, No. 11: pp. 2080-3086, Nov. 2003.

Non-final Office Action pertaining to U.S. Appl. No. 12/643,338 dated Apr. 26, 2012.

International Search Report, Application No. PCT/EP2009/009170 filed Dec. 21, 2009, completion of ISR is Sep. 24, 2010, pp. 1-24.

Dassau, et al., Detection of a Meal Using Continuous Glucose Monitoring, Diabetes Care, vol. 31, No. 2, Feb. 2008, pp. 295-300.

Final Office Action regarding U.S. Appl. No. 12/818,930 mailed Mar. 15, 2013.

Non-final Office Action pertaining to U.S. Appl. No. 12/818,310 dated Sep. 26, 2012.

Final Office Action pertaining to U.S. Appl. No. 12/818,875 dated Sep. 28, 2012.

Non-final Office Action pertaining to U.S. Appl. No. 12/643,415 dated Sep. 13, 2012.

Non-final Office Action pertaining to U.S. Appl. No. 12/818,930 dated Aug. 27, 2012.

Non-final Office Action pertaining to U.S. Appl. No. 13/107,436, dated May 31, 2013.

Final Office Action pertaining to U.S. Appl. No. 12/643,415, dated May 17, 2013.

* cited by examiner

| | 237a | 240a | 256a | | | |
|---|---|---|---|---|---|---|
| | 237b | 240b | 256b | 12/23/2009 8:00 | 1 | |
| | 237c | 240c | 256c | 12/23/2009 9:00 | 2 | 5,1 |
| | 237d | 240d | 256d | 12/23/2009 9:30 | 3 | 5,1 |
| | ... | ... | ... | 12/23/2009 10:00 | <null> | |
| | 237n | 240n | 256n | mm/dd/yyyy hh:mm | n | |

FIG. 4

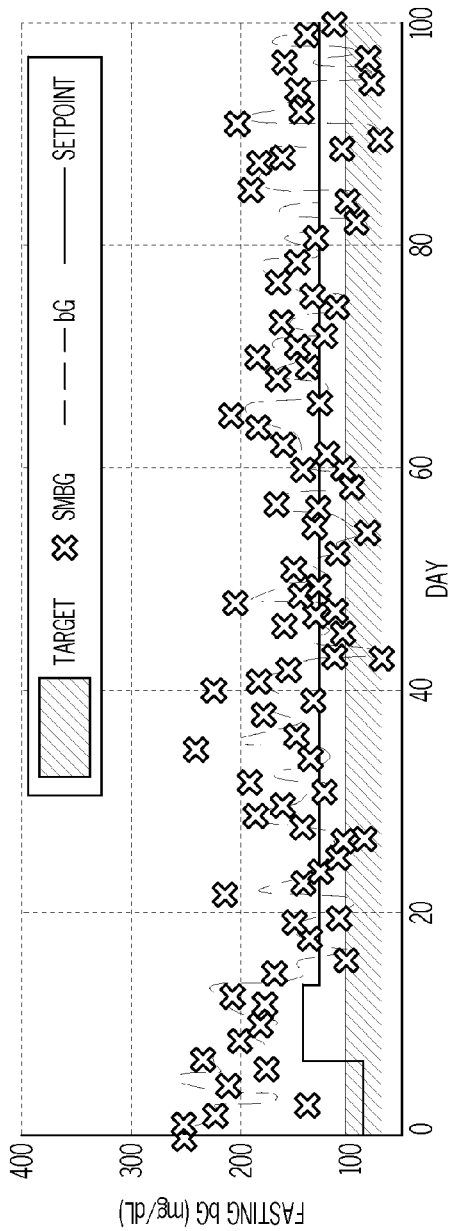
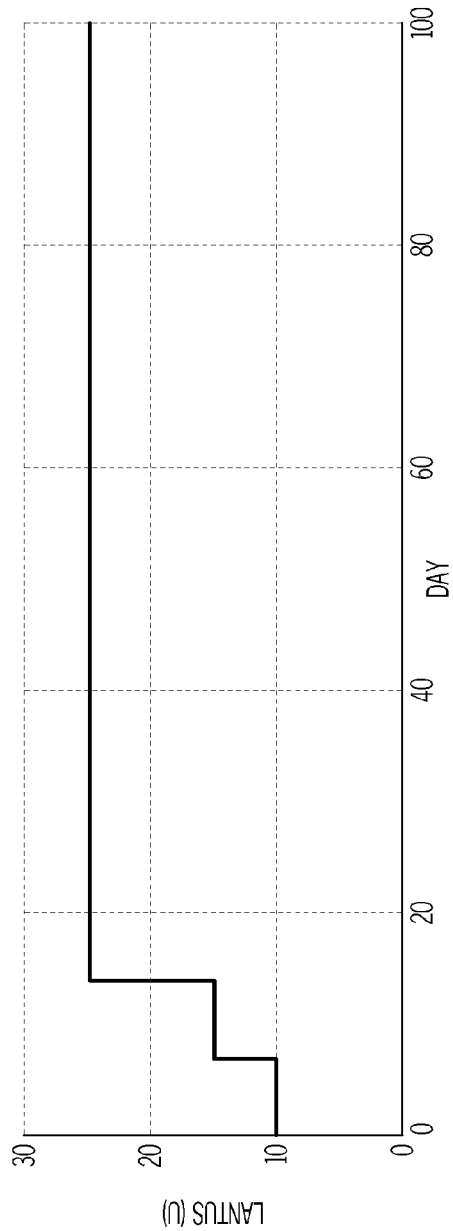
FIG. 11A
FIG. 11B

INSULIN OPTIMIZATION SYSTEMS AND TESTING METHODS WITH ADJUSTED EXIT CRITERION ACCOUNTING FOR SYSTEM NOISE ASSOCIATED WITH BIOMARKERS

TECHNICAL FIELD

Embodiments of the present disclosure relate generally to diabetes management, and particularly to methods and systems for diabetic patients to optimize their administered insulin dosage.

BACKGROUND

Diabetes mellitus is a collection of metabolic diseases characterized by hyperglycemia resulting from inadequate insulin secretion, insulin action, or both. Diabetes manifests itself differently in each person because of each person's unique physiology that interacts with variable health and lifestyle factors such as diet, weight, stress, illness, exercise, and medication intake. Biomarkers are patient biologically derived indicators of biological or pathogenic processes, pharmacologic responses, events or conditions (e.g., aging, disease or illness risk, presence or progression, etc.). For example, a biomarker can be an objective measurement of a variable related to a disease, which may serve as an indicator or predictor of that disease. In the case of diabetes mellitus, such biomarkers include measured values for glucose, lipids, triglycerides, and the like. A biomarker can also be a set of parameters from which to infer the presence or risk of a disease, rather than a measured value of the disease itself. When properly collected and evaluated, biomarkers can provide useful information related to a medical question about the patient, used as part of a medical assessment, as a medical control, and/or for medical optimization.

For diabetes, clinicians generally treat patients according to therapeutic guidelines such as Joslin Diabetes Center & Joslin Clinic, *Clinical Guideline for Pharmacological Management of Type 2 Diabetes* (2007) and Joslin Diabetes Center & Joslin Clinic, *Clinical Guideline for Adults with Diabetes* (2008). The guidelines may specify a desired biomarker value, e.g., a fasting blood glucose value of less than 100 mg/dl.

While guidelines and algorithms have been developed for insulin titration, the exit criterion for titration algorithms is often defined with the same threshold value applied to all patients. However, some biomarker levels (e.g. blood glucose measurements) have high variance, or noise associated with their measurements. Noise or variance may vary from patient to patient. The sources of variance, or noise, can be placed in two categories: system noise and protocol noise. In essence, system noise occurs when the amount of insulin delivered to the diabetic patient differs from the amount actually effective. System noise may be caused by insulin sensitivity i.e., variable physiological effects which vary the effectiveness of insulin from day to day. The protocol noise may result from patient error due to improper physical manipulation of the insulin delivery vehicle e.g., syringe or failure to measure blood glucose at the proper time. All sources of noise can lead to greater risk of adverse events (e.g., hyperglycemic and hypoglycemic events), and system noise in particular causes increased risk due to the difficulty in controlling the internal physiological effects. Consequently, patients with high system noise associated with their biomarker readings should not have the same exit criterion as patients with low levels of system noise It is desirable to include an algorithm which accommodates for system noise in the exit criterion, thereby leading to fewer adverse events.

SUMMARY

It is against the above background that the present testing method embodiments suitable for diabetic patients to optimize their administered insulin dosage are provided. The present disclosure provides a structured approach to alter the exit criterion for insulin titration by quantifying the risk of adverse events (e.g., hyperglycemic and hypoglycemic events), and optimize the insulin titration by minimizing the risk. While in the current disclosure the procedure for altering the exit criterion is presented for fasting blood glucose values in insulin titration, the underlying methodology is broad enough to be applied to a variety of different algorithms and biomarkers.

Embodiments of the disclosure can be implemented, for example, as follows: a paper tool; diabetes software integrated into a collection device such as a blood glucose meter; diabetes software integrated into a personal digital assistant, handheld computer, or mobile phone; diabetes software integrated into a device reader coupled to a computer; diabetes software operating on a computer such as a personal computer; and diabetes software accessed remotely through the internet.

According to one embodiment, a testing method for optimizing an insulin dosage to a patient is provided. A testing method for optimizing an insulin dosage to a diabetic patient comprising collecting at least one sampling set of biomarker data, wherein each sampling set comprises one or more sampling instances recorded over a collection period and each sampling instances comprises one or more biomarker readings, computing a probability distribution function, a hazard function, a risk function, and a risk value for the sampling set of biomarker data wherein, the probability distribution function is calculated to approximate the probability distribution of the biomarker data, the hazard function is a function which yields higher hazard values for biomarker readings in the sampling set indicative of higher risk of complications, the risk function is the product of the probability distribution function and the hazard function, and the risk value is calculated by the integral of the risk function. The testing method further comprises minimizing the risk value by adjusting the diabetic patient's therapy, and exiting the testing method when the risk value for at least one sampling set is minimized to an optimal risk level.

According to another embodiment, a method for guiding a diabetic patient through a testing plan directed to optimizing an administration dosage of insulin is provided, wherein the method utilizes a data processing system. The method comprises instructing the diabetic patient via a display unit to collect one or more sampling sets of biomarker data. The method also comprises computing a probability distribution function, a hazard function, a risk function, and a risk value for the sampling set of biomarker data, and also comprises instructing the patient to adjust the patient's therapy, or exit the testing method if the risk value for at least one sampling set is minimized to an optimal risk level.

According to another embodiment, a collection device configured to guide a diabetic patient through a testing plan directed to optimizing the administration dosage of insulin is provided. The collection device comprises a meter configured to measure one or more selected biomarkers, a processor disposed inside the meter and coupled to memory, wherein the memory comprises collection procedures, and software having instructions that when executed by the processor causes the processor to instruct the diabetic patient to collect one or more sampling sets of biomarker data in accordance with the collection procedures. The software and associated collection procedures also causes the processor to instruct the diabetic patient, compute a probability distribution function, a hazard function, a risk function, and a risk value for the sampling set of biomarker data. The processor further instructs the patient to adjust the patient's therapy, or exit the testing method if the risk value for at least one sampling set is minimized to an optimal risk level.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals.

FIG. 4 shows a depiction in tabular format of a data record embodiment created from using a structured testing method on the collection device of FIG. 3 according to the present invention.

FIGS. 11A and 11B are graphical illustrations showing the adjustment of the target level and the adjustment of the insulin dosage associated with the testing methods for optimizing the titration of insulin using risk minimization according to the present invention.

DETAILED DESCRIPTION

Figure 1:
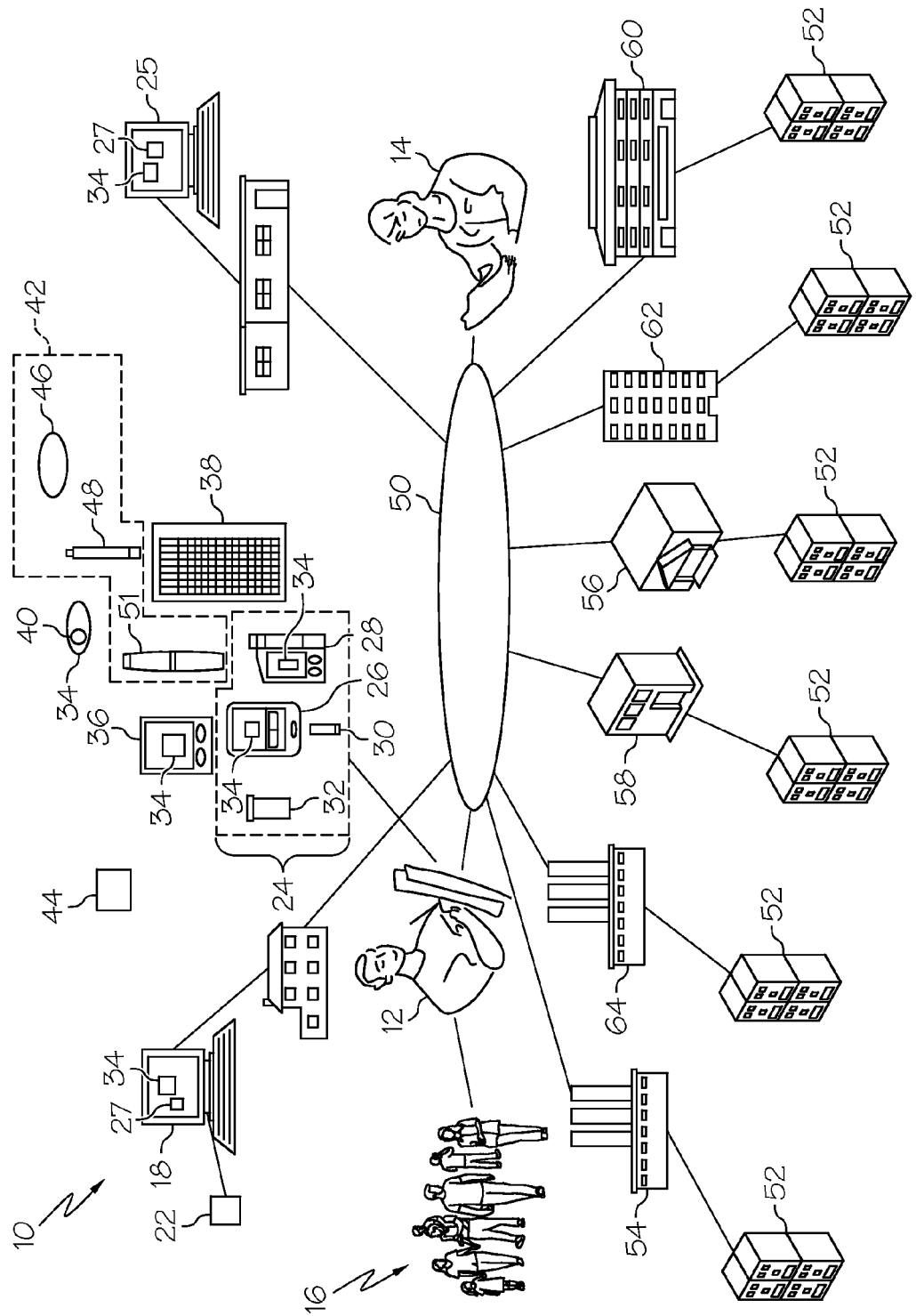
FIG. 1 is a diagram showing a chronic care management system for a diabetic patient and a clinician along with others having an interest in the chronic care management of the patient according to an embodiment of the present invention.

The present invention will be described below relative to various illustrative embodiments. Those skilled in the art will appreciate that the present invention may be implemented in a number of different applications and embodiments and is not specifically limited in its application to the particular embodiments depicted herein. In particular, the present invention will be discussed below in connection with diabetes management via sampling blood, although those of ordinary skill will recognize that the present invention could be modified to be used with other types of fluids or analytes besides glucose, and/or useful in managing other chronic diseases besides diabetes.

As used herein with the various illustrated embodiments described below, the following terms include, but are not limited to, the following meanings.

The term "biomarker" can mean a physiological variable measured to provide data relevant to a patient such as for example, a blood glucose value, an interstitial glucose value, an HbA1c value, a heart rate measurement, a blood pressure measurement, lipids, triglycerides, cholesterol, and the like.

The term "contextualizing" can mean documenting and interrelating conditions that exist or will occur surrounding a collection of a specific biomarker measurement. Preferably, data about documenting and interrelating conditions that exist or will occur surrounding a collection of a specific biomarker are stored together with the collected biomarker data and are linked to it. In particular, a further assessment of the collected biomarker data takes into account the data about documenting and interrelating conditions so that not only the data as such are evaluated but also the link between data to which it is contextualized. The data about documenting and interrelating conditions can include for example information about the time, food and/or exercises which occurs surrounding a collection of a specific biomarker measurement and/or simultaneously thereto. For example, the context of a structured collection procedure according in an embodiment to the present invention can be documented by utilizing entry criterion for verifying a fasting state with the user before accepting a biomarker value during a Basal titration optimization focused testing procedure.

The term "contextualized biomarker data" can mean the information on the interrelated conditions in which a specific biomarker measurement was collected combined with the measured value for the specific biomarker. In particular, the biomarker data are stored together with the information on the interrelated conditions under which a specific biomarker measurement was collected and are linked thereto.

The term "criteria" can mean one or more criterions, and can be at least one or more of a guideline(s), rule(s), characteristic(s), and dimension(s) used to judge whether one or more conditions are satisfied or met to begin, accept, and/or end one or more procedural steps, actions, and/or values.

The term "adherence" can mean that a person following a structured collection procedure performs requested procedural steps appropriately. For example, the biomarker data should be measured under prescribed conditions of the structured collection procedure. If then the prescribed conditions are given for a biomarker measurement the adherence is defined as appropriate. For examples, the prescribed conditions are time related conditions and/or exemplarily can include eating of meals, taking a fasting sample, eating a type of meal with a requested window of time, taking a fasting sample at a requested time, sleeping a minimum amount of time, and the like. The adherence can be defined as appropriate or not appropriate for a structured collection procedure, a group of sample instances, or a single data point of a contextualized biomarker data. Preferably, the adherence can be defined as appropriate or not appropriate by a range of a prescribed condition(s) or by a selectively determined prescribed condition(s). Moreover the adherence can be calculated as a rate of adherence describing in which extent the adherence is given for a structured collection procedure or a single data point in particular of a contextualized biomarker data.

The term "adherence event" can mean when a person executing a structured collection procedure fails to perform a procedural step. For example, if a person did not collect data when requested by the collection device, the adherence is determined as not appropriate resulting in an adherence event. In another example, adherence criteria could be a first criterion for the patient to fast 6 hours and a second criterion for collecting a fasting bG value at a requested time. In this example, if the patient provides the bG sampling at the requested time but fasted only 3 hours before providing, then although the second adherence criterion is met, the first adherence criterion is not, and hence an adherence event for the first criterion would occur.

The term "violation event" is a form of an adherence event in which the person executing the structured collection (testing) procedure (protocol) does not administer a therapeutic at a recommended time, does not administer a recommended amount, or both.

The term "adherence criterion" can include adherence and can mean a basis for comparison (e.g., assessment) of a value/information related to a measured value and/or a calculated value with a defined value/information, or defined range of the values, wherein based on the comparison, data can be accepted with approval and positive reception. Adherence criterion can be applied to contextualized biomarker data so that a biomarker data can be accepted depending on a comparison of the contextualized data regarding the documentation and related conditions that exists or occur, during the collection of the specific biomarker. Adherence criterion can be akin to a sanity check for a given piece of information, or group of information. Preferably, the adherence criterion can be applied to group of data, or information, and can be rejected if the adherence criterion is not fulfilled. In particular, such rejected data are then not used for further calculations that provide a therapy recommendation. Mainly, the rejected data can only be used to assess the adherence and/or to automatically trigger at least one further action. For example, such a triggered action can prompt the user to follow a structured collection procedure, or a single requested action, so that the adherence criterion can be fulfilled.

As used herein, a biomarker, or event value, can be "acceptable" if the user follows the appropriate and recommended steps (i.e., adherence), and, in a preferred embodiment, the resulting data are within a predicted range. For example, before a sample is taken, the acceptance criteria can establish whether the steps leading up to taking of the sample were accomplished. For example, the processor in response to a request displays the question, "Have you been fasting for the last 8 hours?," wherein a "Yes" response received by the processor via the user interface meets the acceptance criterion for this step. In another example, after the sample is taken, the processor can assess the received data for reasonableness using other acceptance criterion(s). For example, based on prior data, a fasting bG sample should be between 120-180 mg/dl, but the received value was of 340 mg/dl, and thus fails such acceptance criteria since it is outside the predefined range for an acceptable value. In such an example, the processor could prompt for an additional sample. If the re-sampling fails too (i.e., not between 120-180 mg/dl), the assessment provided by the processor can be that the patient has not fasted, and, thus, the processor, as instructed by the acceptance criterion upon a failing of the re-sampling, can automatically extend the events in the schedule of events accordingly.

The terms "software" and "program" may be used interchangeably herein.

FIG. 1 shows a chronic care management system 10 for a diabetes patient(s) 12 and a clinician(s) 14 along with others 16 having an interest in the chronic care management of the patient 12. Patient 12, having dysglycemia, may include persons with a metabolic syndrome, pre-diabetes, type 1 diabetes, type 2 diabetes, and gestational diabetes. The others 16 with an interest in the patient's care may include family members, friends, support groups, and religious organizations all of which can influence the patient's conformance with therapy. The patient 12 may have access to a patient computer 18, such as a home computer, which can connect to a public network 50 (wired or wireless), such as the internet, cellular network, etc., and couple to a dongle, docking station, or device reader 22 for communicating with an external portable device, such as a portable collection device 24. An example of a device reader is shown in the manual "Accu-Chek® Smart Pix Device Reader User's Manual" (2008) available from Roche Diagnostics.

The collection device 24 can be essentially any portable electronic device that can function as an acquisition mechanism for determining and storing digitally a biomarker value (s) according to a structured collection procedure, and which can function to run the structured collection procedure and the method of the present invention. Greater details regarding various illustrated embodiments of the structured collection procedure are provided hereafter in later sections. In a preferred embodiment, the collection device 24 can be a self-monitoring blood glucose meter 26 or a continuous glucose monitor 28. An example of a blood glucose meter is the Accu-Chek® Active meter, and the Accu-Chek® Aviva meter described in the booklet "Accu-Chek® Aviva Blood Glucose Meter Owner's Booklet (2007), portions of which are disclosed in U.S. Pat. No. 6,645,368 B1 entitled "Meter and method of using the meter for determining the concentration of a component of a fluid" assigned to Roche Diagnostics Operations, Inc., which is hereby incorporated by reference. An example of a continuous glucose monitor is shown in U.S. Pat. No. 7,389,133 "Method and device for continuous monitoring of the concentration of an analyte" (Jun. 17, 2008) assigned to Roche Diagnostics Operations, Inc., which is hereby incorporated by reference.

In addition to the collection device 24, the patient 12 can use a variety of products to manage his or her diabetes including: test strips 30 carried in a vial 32 for use in the collection device 24; software 34 which can operate on the patient computer 18, the collection device 24, a handheld computing device 36, such as a laptop computer, a personal digital assistant, and/or a mobile phone; and paper tools 38. Software 34 can be pre-loaded or provided either via a computer readable medium 40 or over the public network 50 and loaded for operation on the patient computer 18, the collection device 24, the clinician computer/office workstation 25, and the handheld computing device 36, if desired. In still other embodiments, the software 34 can also be integrated into the device reader 22 that is coupled to the computer (e.g., computers 18 or 25) for operation thereon, or accessed remotely through the public network 50, such as from a server 52.

The patient 12 can also use for certain diabetes therapies additional therapy devices 42 and other devices 44. Additionally, therapy devices 42 can include devices such as an ambulatory infusion pump 46, an insulin pen 48, and a lancing device 51. An example of an ambulatory insulin pump 46 include but not limited thereto the Accu-Chek® Spirit pump described in the manual "Accu-Chek® Spirit Insulin Pump System Pump User Guide" (2007) available from Disetronic Medical Systems AG. The other devices 44 can be medical devices that provide patient data such as blood pressure, fitness devices that provide patient data such as exercise information, and elder care device that provide notification to care givers. The other devices 44 can be configured to communicate with each other according to standards planned by Continua® Health Alliance. These therapy devices can be separate or integrated into the collection devices and data processing devices described herein.

The clinicians 14 for diabetes are diverse and can include e.g., nurses, nurse practitioners, physicians, endocrinologists, and other such health care providers. The clinician 14 typically has access to a clinician computer 25, such as a clinician office computer, which can also be provided with the software 34. A healthcare record system 27, such as Microsoft® HealthVault™ and Google™ Health, may also be used by the patient 12 and the clinician 14 on computers 18, 25 to exchange information via the public network 50 or via other network means (LANs, WANs, VPNs, etc.), and to store information such as collection data from the collection device 24 to an electronic medical record of the patient e.g., EMR 53 (FIG. 2A) which can be provided to and from computer 18, 25 and/or server 52.

Figure 2:
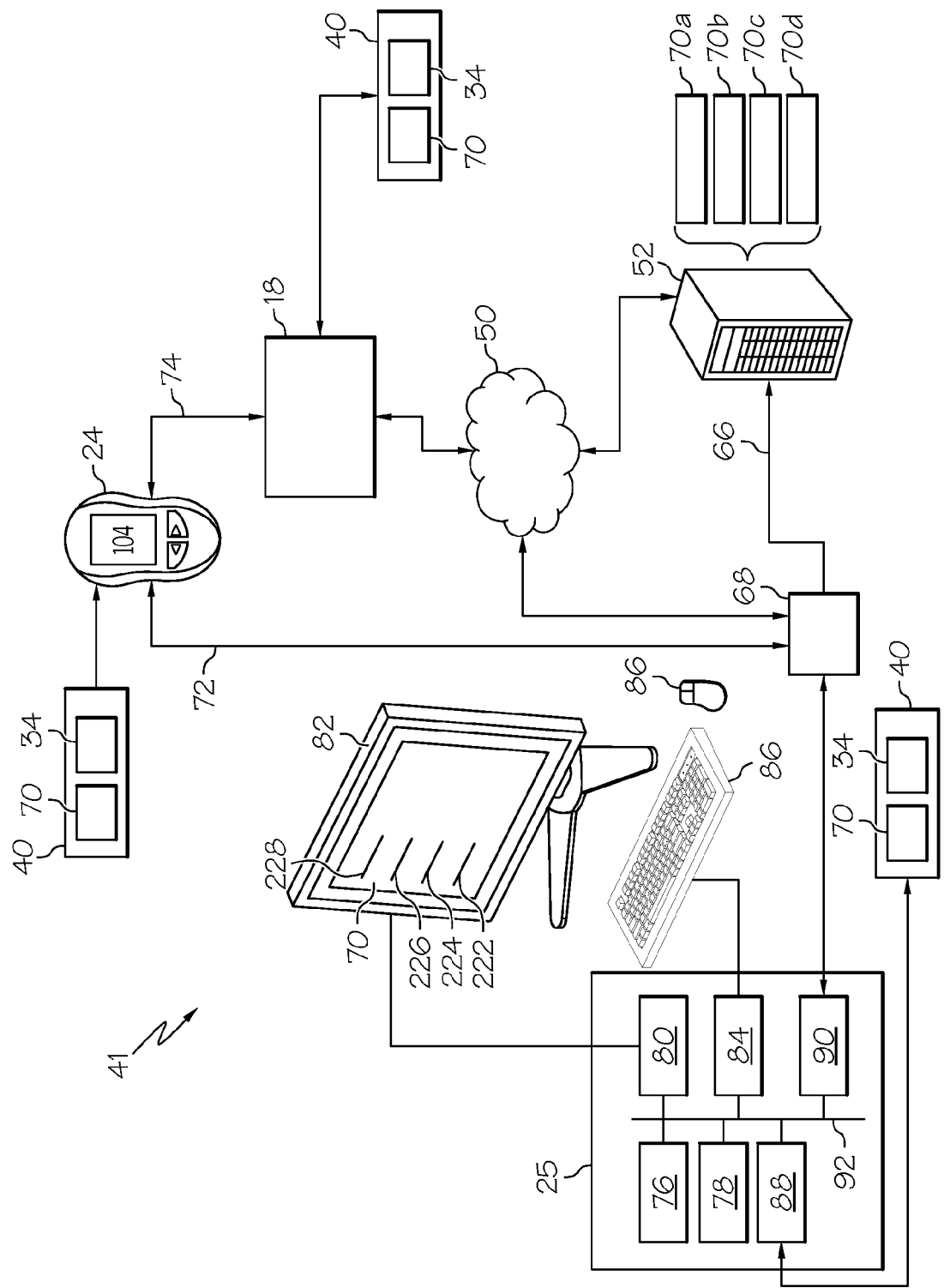
FIGS. 2 and 2A are diagrams showing embodiments of a system suitable for implementing a structured testing method according to an embodiment of the present invention.

Most patients 12 and clinicians 14 can interact over the public network 50 with each other and with others having computers/servers 52. Such others can include the patient's employer 54, a third party payer 56, such as an insurance company who pays some or all of the patient's healthcare expenses, a pharmacy 58 that dispenses certain diabetic consumable items, a hospital 60, a government agency 62, which can also be a payer, and companies 64 providing healthcare products and services for detection, prevention, diagnosis and treatment of diseases. The patient 12 can also grant permissions to access the patient's electronic health record to others, such as the employer 54, the payer 56, the pharmacy 58, the hospital 60, and the government agencies 62 via the healthcare record system 27, which can reside on the clinician computer 25 and/or one or more servers 52. Reference hereafter is also made to FIG. 2.

FIG. 2 shows a system embodiment suitable for implementing a structured testing method according to an embodiment of the present invention, which in another embodiment can be a part of the chronic care management system 10 and communicate with such components, via conventional wired or wireless communication means. The system 41 can include the clinician computer 25 that is in communication with a server 52 as well as the collection device 24. Communications between the clinician computer 25 and the server 52 can be facilitated via a communication link to the public network 50, to a private network 66, or combinations thereof. The private network 66 can be a local area network or a wide are network (wired or wireless) connecting to the public network 50 via a network device 68 such as a (web) server, router, modem, hub, and the likes.

In one embodiment, the server 52 can be a central repository for a plurality of structured collection procedures (or protocols) 70a, 70b, 70c, 70d, in which the details of a few exemplary structured collection procedures are provided in later sections. The server 52, as well as the network device 68, can function also as a data aggregator for completed ones of the structured collection procedures 70a, 70b, 70c, 70d. Accordingly, in such an embodiment, data of a completed collection procedure(s) from a collection device of the patient 12 can then be provided from the server 52 and/or network device 68 to the clinician computer 25 when requested in response to a retrieval for such patient data.

Figure 2A:
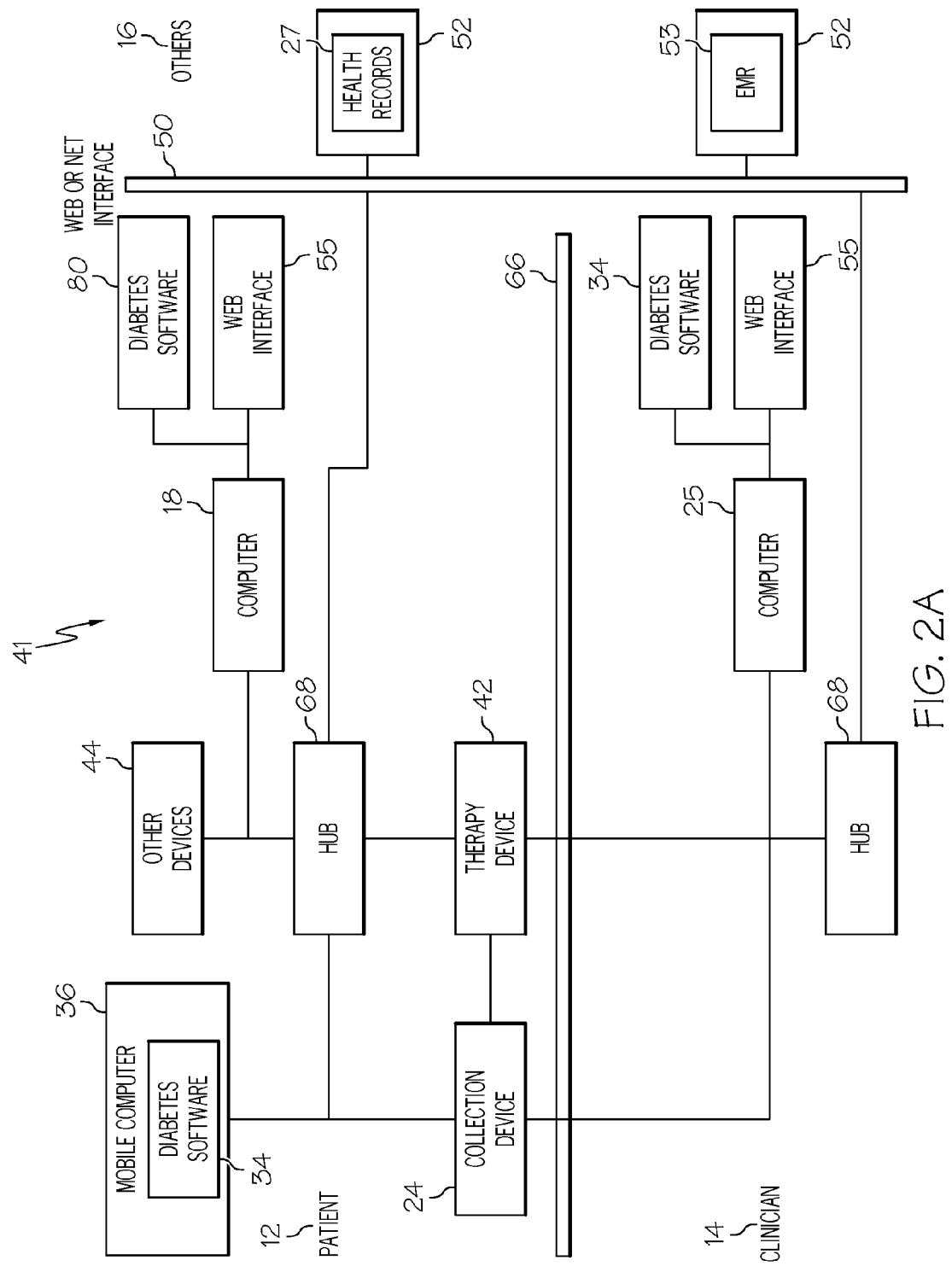

In one embodiment, one or more of the plurality of structured collection procedures 70a, 70b, 70c, 70d on the server 52 can be provided over the public network 50, such as through a secure web interface 55 (FIG. 2A, showing another embodiment of the system 41) implemented on the patient computer 18, the clinician computer 25, and/or the collection device 24. In another embodiment, the clinician computer 25 can serve as the interface (wired or wireless) 72 between the server 52 and the collection device 24. In still another embodiment, the structured collection procedures 70a, 70b, 70c, 70d, as well as software 34, may be provided on a computer readable medium 40 and loaded directed on the patient computer 18, the clinician computer 25, and/or the collection device 24. In still another embodiment, the structured collection procedures 70a, 70b, 70c, 70d may be provided pre-loaded (embedded) in memory of the collection device 24. In still other embodiments, new/updated/modified structured collection procedures 70a, 70b, 70c, 70d may be sent between the patient computer 18, the clinician computer 25, the server 52 and/or the collection device 24 via the public network 50, the private network 66, via a direct device connection (wired or wireless) 74, or combinations thereof. Accordingly, in one embodiment the external devices e.g., computer 18 and 25, can be used to establish a communication link 72, 74 between the collection device 24 and still further electronic devices such as other remote Personal Computer (PC), and/or servers such as through the public network 50, such as the Internet and/or other communication networks (e.g., LANs, WANs, VPNs, etc.), such as private network 66.

Figure 3:
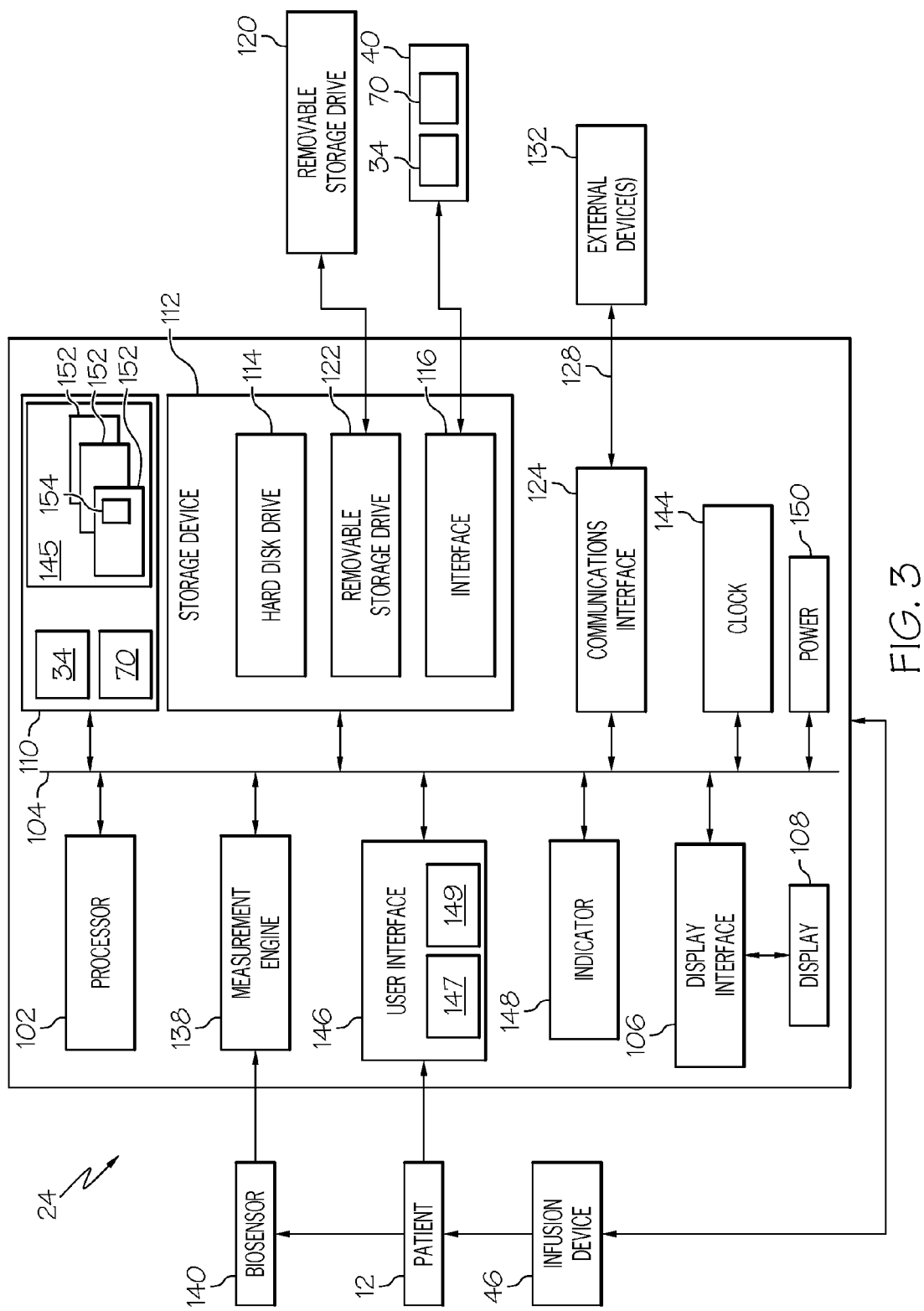
FIG. 3 shows a block diagram of a collection device embodiment according to the present invention.

The clinician computer 25, as a conventional personal computer/workstation, can include a processor 76 which executes programs, such as software 34, and such as from memory 78 and/or computer readable medium 40. Memory 78 can include system memory (RAM, ROM, EEPROM, etc.), and storage memory, such as hard drives and/or flash memory (internal or external). The clinician computer 25 can also include a display driver 80 to interface a display 82 with the processor 76, input/output connections 84 for connecting user interface devices 86, such as a keyboard and mouse (wired or wireless), and computer readable drives 88 for portable memory and discs, such as computer readable medium 40. The clinician computer 25 can further include communication interfaces 90 for connections to the public network 50 and other devices, such as collection device 24 (wired or wireless), and a bus interface 92 for connecting the above mentioned electronic components to the processor 76. Reference hereafter is now made to FIG. 3.

FIG. 3 is a block diagram conceptually illustrating the portable collection device 24 depicted in FIG. 2. In the illustrated embodiment, the collection device 24 can include one or more microprocessors, such as processor 102, which may be a central processing unit comprising at least one more single or multi-core and cache memory, which can be connected to a bus 104, which may include data, memory, control and/or address buses. The collection device 24 can include the software 34, which provides instruction codes that causes a processor 102 of the device to implement the methods of the present invention that are discussed hereafter in later sections. The collection device 24 may include a display interface 106 providing graphics, text, and other data from the bus 104 (or from a frame buffer not shown) for display on a display 108. The display interface 106 may be a display driver of an integrated graphics solution that utilizes a portion of main memory 110 of the collection device 24, such as random access memory (RAM) and processing from the processor 102 or may be a dedicated graphic processing unit. In another embodiment, the display interface 106 and display 108 can additionally provide a touch screen interface for providing data to the collection device 24 in a well-known manner.

Main memory 110 in one embodiment can be random access memory (RAM), and in other embodiments may include other memory such as a ROM, PROM, EPROM or EEPROM, and combinations thereof. In one embodiment, the collection device 24 can include secondary memory 112, which may include, for example, a hard disk drive 114 and/or a computer readable medium drive 116 for the computer readable medium 40, representing for example, at least one of a floppy disk drive, a magnetic tape drive, an optical disk drive, a flash memory connector (e.g., USB connector, Firewire connector, PC card slot), etc. The drive 116 reads from and/or writes to the computer readable medium 40 in a well-known manner. Computer readable medium 40, represents a floppy disk, magnetic tape, optical disk (CD or DVD), flash drive, PC card, etc. which is read by and written to by the drive 116. As will be appreciated, the computer readable medium 40 can have stored therein the software 34 and/or structured collection procedures 70a, 70b, 70c, and 70d as well as data resulting from completed collections performed according to one or more of the collection procedures 70a, 70b, 70c, and 70d.

In alternative embodiments, secondary memory 112 may include other means for allowing the software 34, the collection procedures 70a, 70b, 70c, 70d, other computer programs or other instructions to be loaded into the collection device 24. Such means may include, for example, a removable storage unit 120 and an interface connector 122. Examples of such removable storage units/interfaces can include a program cartridge and cartridge interface, a removable memory chip (e.g., ROM, PROM, EPROM, EEPROM, etc.) and associated socket, and other removable storage units 120 (e.g. hard drives) and interface connector 122 which allow software and data to be transferred from the removable storage unit 120 to the collection device 24.

The collection device 24 in one embodiment can include a communication module 124. The communication module 124 allows software (e.g., the software 34, the collection procedures 70a, 70b, 70c, and 70d) and data (e.g., data resulting from completed collections performed according to one or more of the collection procedures 70a, 70b, 70c, and 70d) to be transferred between the collection device 24 and an external device(s) 126. Examples of communication module 124 may include one or more of a modem, a network interface (such as an Ethernet card), a communications port (e.g., USB, Firewire, serial, parallel, etc.), a PC or PCMCIA slot and card, a wireless transceiver, and combinations thereof. The external device(s) 126 can be the patient computer 18, the clinician computer 25, the handheld computing devices 36, such as a laptop computer, a personal digital assistance (PDA), a mobile (cellular) phone, and/or a dongle, a docking station, or device reader 22. In such an embodiment, the external device 126 may provided and/or connect to one or more of a modem, a network interface (such as an Ethernet card), a communications port (e.g., USB, Firewire, serial, parallel, etc.), a PCMCIA slot and card, a wireless transceiver, and combinations thereof for providing communication over the public network 50 or private network 66, such as with the clinician computer 25 or server 52. Software and data transferred via communication module 124 can be in the form of wired or wireless signals 128, which may be electronic, electromagnetic, optical, or other signals capable of being sent and received by communication module 124. For example, as is known, signals 128 may be sent between communication module 124 and the external device(s) 126 using wire or cable, fiber optics, a phone line, a cellular phone link, an RF link, an infrared link, other communications channels, and combinations thereof. Specific techniques for connecting electronic devices through wired and/or wireless connections (e.g. USB and Bluetooth, respectively) are well known in the art.

In another embodiment, the collection device 24 can be used with the external device 132, such as provided as a handheld computer or a mobile phone, to perform actions such as prompt a patient to take an action, acquire a data event, and perform calculations on information. An example of a collection device combined with such an external device 126 provided as a hand held computer is disclosed in U.S. patent application Ser. No. 11/424,757 filed Jun. 16, 2006 entitled "System and method for collecting patient information from which diabetes therapy may be determined," assigned to Roche Diagnostics Operations, Inc., which is hereby incorporated by reference. Another example of a handheld computer is shown in the user guide entitled "Accu-Chek® Pocket Compass Software with Bolus Calculator User Guide" (2007) available from Roche Diagnostics.

In the illustrative embodiment, the collection device 24 can provide a measurement engine 138 for reading a biosensor 140. The biosensor 140, which in one embodiment is the disposable test strip 30 (FIG. 1), is used with the collection device 24 to receive a sample such as for example, of capillary blood, which is exposed to an enzymatic reaction and measured by electrochemistry techniques, optical techniques, or both by the measurement engine 138 to measure and provide a biomarker value, such as for example, a blood glucose level. An example of a disposable test strip and measurement engine is disclosed in U.S. Patent Pub. No. 2005/0016844 A1 "Reagent stripe for test strip" (Jan. 27, 2005), and assigned to Roche Diagnostics Operations, Inc., which is hereby incorporated by reference. In other embodiments, the measurement engine 138 and biosensor 140 can be of a type used to provide a biomarker value for other types of sampled fluids or analytes besides or in addition to glucose, heart rate, blood pressure measurement, and combinations thereof. Such an alternative embodiment is useful in embodiments where values from more then one biomarker type are requested by a structured collection procedure according to the present invention. In still another embodiment, the biosensor 140 may be a sensor with an indwelling catheter(s) or being a subcutaneous tissue fluid sampling device(s), such as when the collection device 24 is implemented as a continuous glucose monitor (CGM) in communication with an infusion device, such as pump 46 (FIG. 1). In still another embodiments, the collection device 24 can be a controller implementing the software 34 and communicating between the infusion device (e.g., ambulatory infusion pump 46 and electronic insulin pen 48) and the biosensor 140.

Data, comprising at least the information collected by the biosensor 140, is provided by the measurement engine 138 to the processor 102 which may execute a computer program stored in memory 110 to perform various calculations and processes using the data. For example, such a computer program is described by U.S. patent application Ser. No. 12/492,667, filed Jun. 26, 2009, titled "Method, System, and Computer Program Product for Providing Both an Estimated True Mean Blood Glucose Value and Estimated Glycated Hemoglobin (HbA1C) Value from Structured Spot Measurements Of Blood Glucose," and assigned to Roche Diagnostics Operations, Inc., which is hereby incorporated by reference. The data from the measurement engine 138 and the results of the calculation and processes by the processor 102 using the data is herein referred to as self-monitored data. The self-monitored data may include, but not limited thereto, the glucose values of a patient 12, the insulin dose values, the insulin types, and the parameter values used by processor 102 to calculate future glucose values, supplemental insulin doses, and carbohydrate supplement amounts as well as such values, doses, and amounts. Such data along with a date-time stamp 169 for each measured glucose value and administered insulin dose value is stored in a data file 145 of memory 110 and/or 112. An internal clock 144 of the collection device 24 can supply the current date and time to processor 102 for such use.

The collection device 24 can further provide a user interface 146, such as buttons, keys, a trackball, touchpad, touch screen, etc. for data entry, program control and navigation of selections, choices and data, making information requests, and the likes. In one embodiment, the user interface 146 can comprises one or more buttons 147, 149 for entry and navigation of the data provided in memory 110 and/or 112. In one embodiment, the user can use one or more of buttons 147, 149 to enter (document) contextualizing information, such as data related to the everyday lifestyle of the patient 12 and to acknowledge that prescribed tasks are completed. Such lifestyle data may relate to food intake, medication use, energy levels, exercise, sleep, general health conditions and overall well-being sense of the patient 12 (e.g., happy, sad, rested, stressed, tired, etc.). Such lifestyle data can be recorded into memory 110 and/or 112 of the collection device 24 as part of the self-monitored data via navigating through a selection menu displayed on display 108 using buttons 147, 149 and/or via a touch screen user interface provided by the display 108. It is to be appreciated that the user interface 146 can also be used to display on the display 108 the self monitored data or portions thereof, such as used by the processor 102 to display measured glucose levels as well as any entered data.

In one embodiment, the collection device 24 can be switched on by pressing any one of the buttons 147, 149 or any combination thereof. In another embodiment, in which the biosensor 140 is a test-strip, the collection device 24 can be automatically switched on when the test-strip is inserted into the collection device 24 for measurement by the measurement engine 138 of a glucose level in a sample of blood placed on the test-strip. In one embodiment, the collection device 24 can be switched off by holding down one of the buttons 147, 149 for a pre-defined period of time, or in another embodiment can be shut down automatically after a pre-defined period of non-use of the user interface 146.

An indicator 148 can also be connected to processor 102, and which can operate under the control of processor 102 to emit audible, tactile (vibrations), and/or visual alerts/reminders to the patient of daily times for bG measurements and events, such as for example, to take a meal, of possible future hypoglycemia, and the likes. A suitable power supply 150 is also provided to power the collection device 24 as is well known to make the device portable.

As mentioned above previously, the collection device 24 may be pre-loaded with the software 34 or by provided therewith via the computer readable medium 40 as well as received via the communication module 124 by signal 128 directly or indirectly though the external device 132 and/or network 50. When provided in the latter matter, the software 34 when received by the processor 102 of the collection device 24 is stored in main memory 110 (as illustrated) and/or secondary memory 112. The software 34 contains instructions, when executed by the processor 102, enables the processor to perform the features/functions of the present invention as discussed herein in later sections. In another embodiment, the software 34 may be stored in the computer readable medium 40 and loaded by the processor 102 into cache memory to cause the processor 102 to perform the features/functions of the invention as described herein. In another embodiment, the software 34 is implemented primarily in hardware logic using, for example, hardware components such as application specific integrated circuits (ASICs). Implementation of the hardware state machine to perform the feature/functions described herein will be apparent to persons skilled in the relevant art(s). In yet another embodiment, the invention is implemented using a combination of both hardware and software.

In an example software embodiment of the invention, the methods described hereafter can be implemented in the C++ programming language, but could be implemented in other programs such as, but not limited to, Visual Basic, C, C++, Java or other programs available to those skilled in the art. In still other embodiment, the program 34 may be implemented using a script language or other proprietary interpretable language used in conjunction with an interpreter. Reference hereafter is also made to FIG. 4.

FIG. 4 depicts in tabular form a data file 145 containing data records 152 of self-monitored data 154 resulting from a structured collection procedure according to an embodiment of the present invention. The data records 152 (e.g., rows) along with the self-monitoring data 154 (e.g., various one of the columns) can also provide associated therewith contextual information 156 (e.g., other various ones of the columns as well as via row and column header information). Such contextual information 156 can be collected either automatically, such as for example via input received automatically from the measurement engine, the biosensor, and/or any one of the other devices, or via input received from the user interface which was manually enter by the patient in response to a collection request (e.g., a question displayed by the processor 102 on the display 108) during the structured collection procedure. Accordingly, as such contextual information 156 can be provided with each data record 152 in a preferred embodiment, such information is readily available to a physician and no further collection of such information is necessarily needed to be provided again by the patient either manually or orally after completing the structured collection procedure. In another embodiment, if such contextual information 156 and/or additional contextual information is collected after completion of a structured collection procedure according to the present invention, such information may be provided in the associated data file and/or record 145, 152 at a later time such as via one of the computers 18, 25. Such information would then be associated with the self-monitored data in the data file 145, and thus would not need to be provided again orally or manually. Such a process in the latter embodiment may be needed in the situation where the structured collection procedure is implemented as or partly as a paper tool 38 which is used with a collection device incapable of running the software 34 implementing such a structured collection procedure.

It is to be appreciated that the date file 145 (or portions thereof, such as only the self-monitored data 154) can be sent/downloaded (wired or wireless) from the collection device 24 via the communication module 124 to another electronic device, such the external device 132 (PC, PDA, or cellular telephone), or via the network 50 to the clinician computer 25. Clinicians can use diabetes software provided on the clinician computer 25 to evaluate the received self-monitored data 154 as well as the contextual information 156 of the patient 12 for therapy results. An example of some of the functions which may be incorporated into the diabetes software and which is configured for a personal computer is the Accu-Chek® 360 Diabetes Management System available from Roche Diagnostics that is disclosed in U.S. patent application Ser. No. 11/999,968 filed Dec. 7, 2007, titled "METHOD AND SYSTEM FOR SETTING TIME BLOCK," and assigned to Roche Diagnostics Operations, Inc., which is hereby incorporated by reference.

In a preferred embodiment, the collection device 24 can be provided as portable blood glucose meter, which is used by the patient 12 for recording self-monitored data comprising insulin dosage readings and spot measured glucose levels. Examples of such bG meters as mentioned above previously include but are not limited to, the Accu-Chek® Active meter and the Accu-Chek® Aviva system both by Roche Diagnostics, Inc. which are compatible with the Accu-Chek® 360° Diabetes management software to download test results to a personal computer or the Accu-Chek® Pocket Compass Software for downloading and communication with a PDA. Accordingly, it is to be appreciated that the collection device 24 can include the software and hardware necessary to process, analyze and interpret the self monitored data in accordance with predefined flow sequences (as described below in detail) and generate an appropriate data interpretation output. In one embodiment, the results of the data analysis and interpretation performed upon the stored patient data by the collection device 24 can be displayed in the form of a report, trend-monitoring graphs, and charts to help patients manage their physiological condition and support patient-doctor communications. In other embodiments, the bG data from the collection device 24 may be used to generated reports (hardcopy or electronic) via the external device 132 and/or the patient computer 18 and/or the clinician computer 25.

The collection device 24 can further provide the user and/or his or her clinician with at least one or more of the possibilities comprising: a) editing data descriptions, e.g. the title and description of a record; b) saving records at a specified location, in particular in user-definable directories as described above; c) recalling records for display; d) searching records according to different criteria (date, time, title, description etc.); e) sorting records according to different criteria (e.g., values of the bG level, date, time, duration, title, description, etc.); f) deleting records; g) exporting records; and/or h) performing data comparisons, modifying records, excluding records as is well known.

As used herein, lifestyle can be described in general as a pattern in an individual's habits such as meals, exercise, and work schedule. The individual additionally may be on medications such as insulin therapy or orals that they are required to take in a periodic fashion. Influence of such action on glucose is implicitly considered by the present invention.

It is to be appreciated that the processor 102 of the collection device 24 can implement one or more structured collection procedures 70 provided in memory 110 and/or 112. Each structured collection procedure 70 in one embodiment can be stand-alone software, thereby providing the necessary program instructions which when executed by the processor 102 causes the processor to perform the structured collection procedure 70 as well as other prescribed functions. In other embodiments, each structured collection procedure 70 can be part of the software 34, and can be then be selectively executed by the processor 102 either via receiving a selection from a menu list provided in the display 108 from the user interface 146 in one embodiment or via activation of a particular user interface, such as a structured collection procedure run mode button (not shown) provided to the collection device 24 in another embodiment. It is to be appreciated that the software 34, likewise, provides the necessary program instructions which when executed by the processor 102 causes the processor to perform the structured collection procedure 70 as well as other prescribed functions of the software 34 discussed herein. One suitable example of having a selectable structured collection procedure provided as a selectable mode of a collection meter is disclosed by in U.S. patent application Ser. No. 12/491,523, filed Jun. 25, 2009, titled "Episodic Blood Glucose Monitoring System With An Interactive Graphical User Interface And Methods Thereof," assigned to Roche Diagnostics Operations, Inc., which is hereby incorporated by reference.

In still another embodiment, a command instruction can be sent from the clinician computer 25 and received by the processor 102 via the communication module 124, which places the collection device 24 in a collection mode which runs automatically the structured collection procedure 70. Such a command instruction may specify which of the one or more structured collection procedures to run and/or provide a structured collection procedure to run. In still another embodiment, a list of defined medical use cases or medical questions can be presented on the display 108 by the processor 102, and a particular structured collection procedure 70 can be automatically chosen by the processor 102 from a plurality of structured collection procedures (e.g., procedures 70a, 70b, 70c, and 70d) depending on the selection of the defined medical use cases or medical questions received by the processor 102 via the user interface 146.

In still another embodiment, after selection, the structured collection procedure(s) 70 can be provided through the computer readable medium e.g., 40 and loaded by the collection device 24, downloaded from computer 18 or 25, the other device(s) 132, or server 52. Server 52, for example, may be a healthcare provider or company providing such pre-defined structured collection procedures 70 for downloading according to a selected defined medical use case or question. It is to be appreciated that the structured collection procedure(s) 70 may be developed by a healthcare company (e.g. company 64) and implemented via the public network 50 through a webpage and/or made available for downloading on server 52, such as illustrated in FIG. 2. In still other embodiments, notices that a new structured collection procedure 70 is available for use on the collection device 24 to help address a particular use case/medical question that a user (e.g., healthcare provider and patient) may have can be provided in any standard fashion, such for via postal letters/cards, email, text messaging, tweets, and the likes.

In some embodiments, as mentioned above previously, a paper tool 38 can perform some of the functions provided by the diabetes software 34. An example of some of the functions which may be incorporated into the diabetes software 34 and which is configured as a paper tool 38 is the Accu-Chek® 360 View Blood Glucose Analysis System paper form available from Roche Diagnostics also disclosed in U.S. patent application Ser. No. 12/040,458 filed Feb. 29, 2007 entitled "Device and method for assessing blood glucose control," assigned to Roche Diagnostic Operations, Inc., which is hereby incorporated by reference.

In still another embodiment, the software 34 can be implemented on the continuous glucose monitor 28 (FIG. 1). In this manner, the continuous glucose monitor 28 can be used to obtain time-resolved data. Such time-resolved data can be useful to identify fluctuations and trends that would otherwise go unnoticed with spot monitoring of blood glucose levels and standard HbA1c tests. Such as, for example, low overnight glucose levels, high blood glucose levels between meals, and early morning spikes in blood glucose levels as well as how diet and physical activity affect blood glucose along with the effect of therapy changes.

In addition to collection device 24 and software 34, clinicians 14 can prescribe other diabetes therapy devices for patients 12 such as an ambulatory insulin pump 46 as well as electronically based insulin pen 48 (FIG. 1). The insulin pump 46 typically includes configuration software such as that disclosed in the manual "Accu-Chek® Insulin Pump Configuration Software" also available from Disetronic Medical Systems AG. The insulin pump 46 can record and provide insulin dosage and other information, as well as the electronically based insulin pen 48, to a computer, and thus can be used as another means for providing biomarker data as requested by the structured collection procedure 70 (FIG. 2) according to the present invention.

It is to be appreciated that, and as mentioned above previously, one or more of the method steps discussed hereafter can be configured as a paper tool 38 (FIG. 1), but preferably all the method steps are facilitated electronically on system 41 (FIG. 2) or on any electronic device/computer, such as collection device 24, having a processor and memory as a program(s) residing in memory. As is known, when a computer executes the program, instructions codes of the program cause the processor of the computer to perform the method steps associated therewith. In still other embodiments, some or all of the method steps discussed hereafter can be configured on computer readable medium 40 storing instruction codes of a program that, when executed by a computer, cause the processor of the computer to perform the method steps associated therewith. These method steps are now discussed in greater detail hereafter with reference made to FIGS. 5-12B.

Testing Method Embodiments for Optimizing the Titration of Insulin

Figure 5:
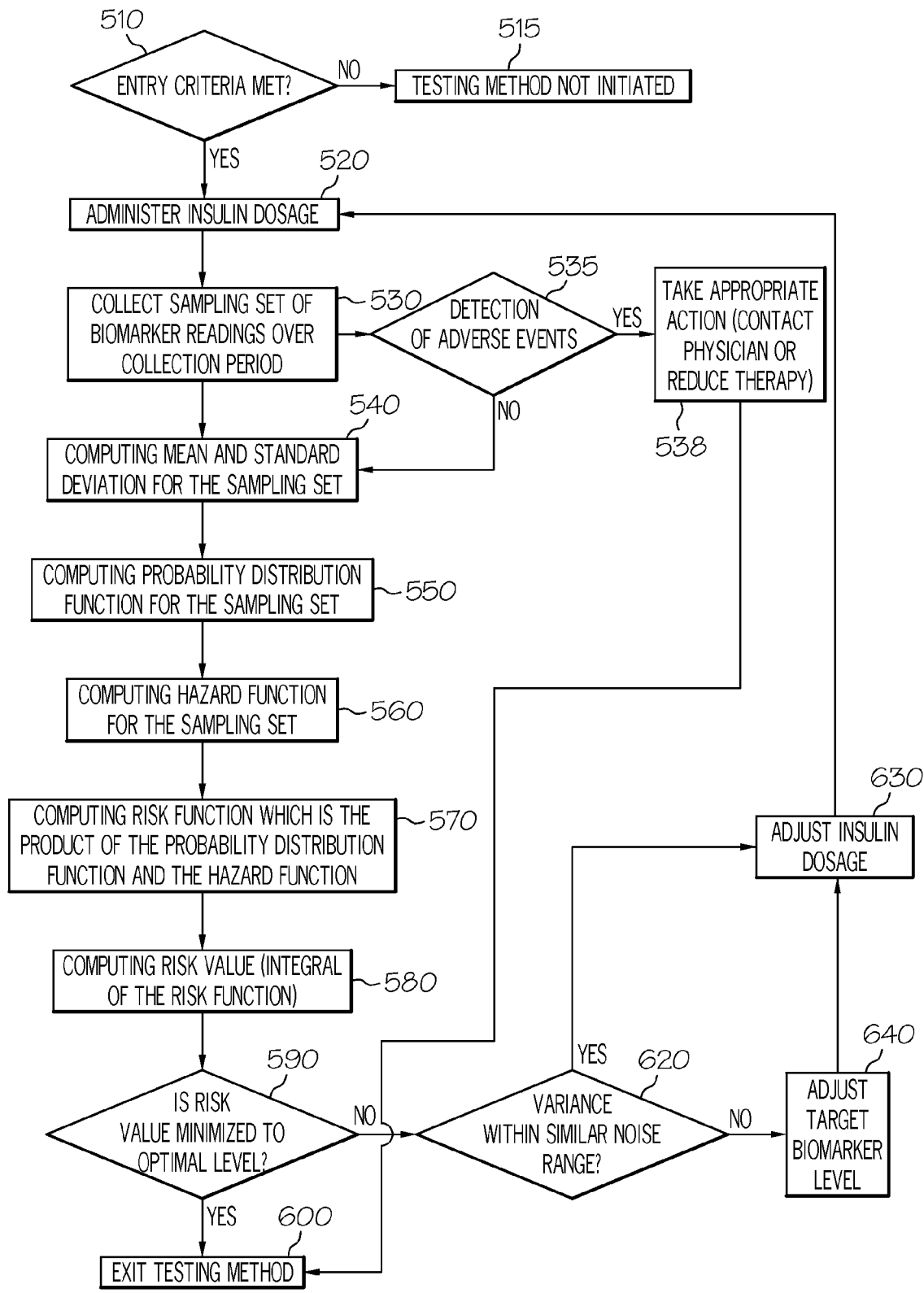
FIG. 5 shows a flow chart depicting a testing method for optimizing the titration of insulin using risk minimization according to the present invention.
Figure 6:
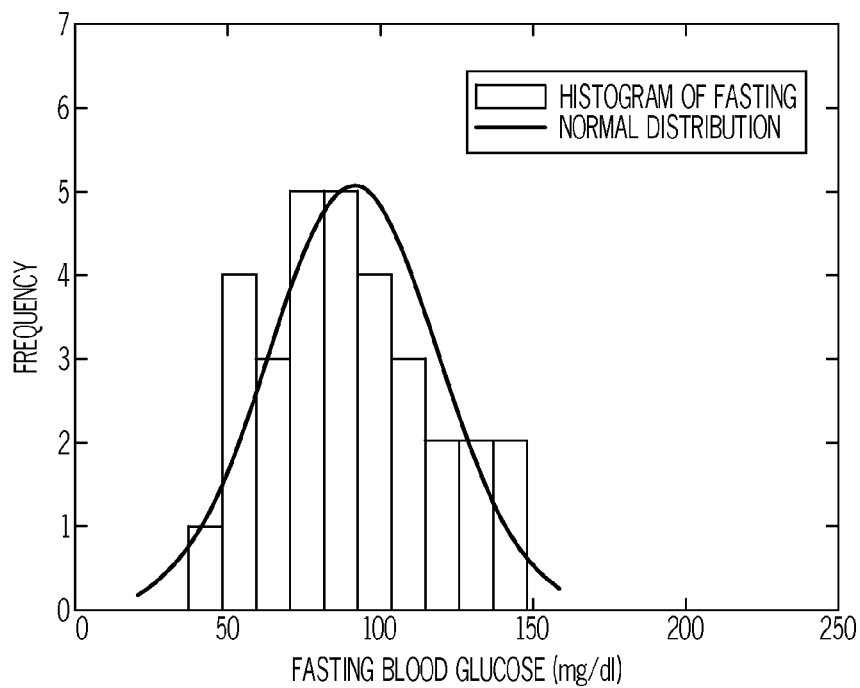
FIG. 6 is a histogram depicting a normal probability distribution of fasting blood glucose biomarker readings according to the present invention.

FIG. 5 is an exemplary testing method embodiment for optimizing the titration of insulin dosage, which thereby yields dosages of insulin which maintain biomarker levels within a desired range. The titrated insulin may be basal insulin. Upon starting the testing plan, the dosage of insulin is typically the initial prescribed dosage, for example, the initial prescribed dosage listed on the package. However, other dosages are contemplated depending on what stage of the testing plan, as the entry criteria may be considered before every biomarker reading. Consequently, the initial dosage may be an adjusted dosage above the initial prescribed dosage, the maximum allowable dosage, or even the optimized dosage. It is contemplated that the testing plan may be used to obtained the optimized insulin value, or may be used post-optimization to verify that the insulin dosage is still optimal.

Referring again to FIG. 5, the testing methods may optionally include the consideration of entry criteria 510 before beginning collection of the biomarker data. It is contemplated that the user, the healthcare provider, or both may determine whether the entry criteria are met. The entry criteria, which in some embodiments may be established by the healthcare provider, may relate to the age, weight, and medical history of the diabetic patient. Consequently, the testing method may require a diabetic patient to receive a check-up or physical to ensure the diabetic patient satisfies the entry criteria. For instance, the entry criteria may specify the fasting plasma glucose (FPG) level or glycolated hemoglobin level as determined by the HbA1c test. The normal range for the HbA1c test is between 4-6% for people without diabetes, so the entry criteria may require values above about 6%, or in an exemplary embodiment, between about 7.5% to about 10%. As an additional example of entry criteria, a fasting plasma glucose level of at least about 140 mg/dl is required. The entry criteria may also set requirements on weight or Body Mass Index (BMI). For example, the required BMI may be greater than about 25 kg/m2, or between about 26 kg/m2 to about 40 kg/m2. Additionally, the entry criteria may specify a desired age range (e.g., 30-70) or the number of years afflicted with diabetes (e.g., at least 2 years). Moreover, while it is contemplated that the testing method is applicable to persons afflicted all types of diabetes, the entry criteria may limit the testing method to type 2 diabetics. Furthermore, the entry criteria may center on the current diabetes treatment regimen of the diabetic patient. For example, the entry criteria may require that the treatment regimen for the diabetic patient be limited to oral anti-diabetes medication i.e., no injected insulin. Additionally, the entry criteria may require that the diabetic patient not be ill or under stress.

If the entry criteria are not met, the testing plan will not be initiated 515 in that optional embodiment. The diabetic patient or healthcare provider may determine whether the entry criteria have been met, or the data processor may determine whether criteria have been met. If the entry criteria are met 510, then the diabetic patient may commence with the testing plan. However, in some embodiments, it may be required for the diabetic patient to satisfy adherence criterion before the collection of biomarkers or the administration of insulin.

Like other instructions provided to the user throughout the testing plan, the entry criteria may be provided to the diabetic patient via a paper instruction form, or a display unit on a data processing device or microprocessor 102 as shown in FIG. 3. The data processing devices may be any electronic device described above. In one or more embodiments, the data processing device may be a computer or a blood glucose meter with a data processor and memory units therein. The data processing device may prompt the diabetic patient to answer medical questions, wherein the answers to the medical questions are used by the device to determine compliance with the entry criteria or adherence criteria, and may inform the diabetic patient of the failure to comply with the entry criteria, or adherence criteria. For example, the data processing device may inform a diabetic patient if subsequent sampling instances are not taken around the same time as the first sampling instance, which is a failure to meet an adherence criterion. The patient can record sampling instances or answer medical questions by entering the data event directly into a device or computer, wherein the processor 102 can store the information and provide additional analysis depending on the parameters of the testing method.

Referring again to FIG. 5, the diabetic patient may begin collection of one or more sampling sets of biomarker data 530. Each sampling set comprises one or more sampling instances recorded over a collection period. Each sampling instance comprises one or more biomarker readings. The collection period for the sampling set may be defined as multiple sampling instances within a day, multiple sampling instances within a week, multiple sampling instances within consecutive weeks, or multiple sampling instances on consecutive days within a week. The biomarker may relate to the levels of glucose, triglycerides, low density lipids, and high density lipids. In one exemplary embodiment, the biomarker reading is a blood glucose reading, specifically a fasting blood glucose reading. In addition to the biomarker reading, each sampling instance may comprise the biomarker reading and other contextual data associated with the biomarker reading, wherein the contextual data is selected from the group consisting of the time of collection, the date of collection, the time when the last meal was consumed, the recommended dose of insulin, and combinations thereof.

After the sampling set of biomarker data is obtained, the data is analyzed to determine if there are any adverse events or a risk of an adverse event. If the data indicates an adverse event 535, then the healthcare provider may be notified, the insulin dosage may be reduced, or both 538, and then the testing plan may be exited. Other patient actions are also contemplated. If there is no adverse event recorded, the probability distribution for the data is estimated. In alternative embodiments, adverse events may also be evaluated when any biomarker readings indicative of an adverse event are received, not just at the end of a sample set. In this embodiment, when an adverse event is detected, the healthcare provider may be notified immediately, not just after the entire sampling set is recorded.

In one embodiment as shown in FIG. 5, the mean and the standard deviation for the sampling set is computed 540 to obtain the probability distribution function; however, other methods (e.g., a kernel density estimator) may be used to calculate the probability distribution function. It is contemplated that the kernel density estimator could consider the current completed sampling set, a portion of the sampling set, or multiple sampling sets. By considering the standard deviation in addition to the mean, the probability distribution can at least in part account for the noise characteristics of the biomarker values during insulin titration. To produce the probability function, a normal distribution of the data is created as graphically depicted in the histogram of FIG. 6.

A normal distribution can be fitted to the data by calculating the current therapy mean and standard deviation for the sampling set of biomarker data over the collection period. The resulting probability distribution function p(B) for a normal distribution is defined in the following equation $p(B)=N(\overline{B}, \sigma_B)$ wherein B is a biomarker reading or sampling instance, $\overline{B}$ is the mean of sampling set of biomarker data defined by the equation $$\overline{B} = \frac{1}{n}\sum_{i=1}^{n} B_i,$$

and $\sigma_B$ is the standard deviation defined by the equation $$\sigma_B^2 = \frac{1}{n-1}\sum_{i=1}^{n}(B_i - \overline{B})^2.$$

The probability distribution of the biomarkers may also be calculated using kernel density estimators. These estimators can represent data that is not normally distributed such as bi-modal distributions.

$$p(B) = \frac{\frac{1}{n}\sum_{i=1}^{n}\alpha(t_i)k(B_i, B)}{\sum_{i=1}^{n}\alpha(t_i)}$$

$$a(t) = e^{-t/\beta_0}$$

$$k(B_i, B) = \frac{1}{\sqrt{2\pi\sigma^2}}e^{-\frac{(B-B_0)}{2\sigma^2}}$$

Referring again to FIG. 5, a hazard function for the sampling set of biomarker data is then calculated 560. The conceptual basis for the hazard function lies in penalizing values that are associated with greater patient risk. The hazard function yields higher hazard values for biomarker readings in the sampling set indicative of complications (for example, hyperglycemia or hypoglycemia) and yields hazard values at or near zero at the target biomarker level.

Figure 7:
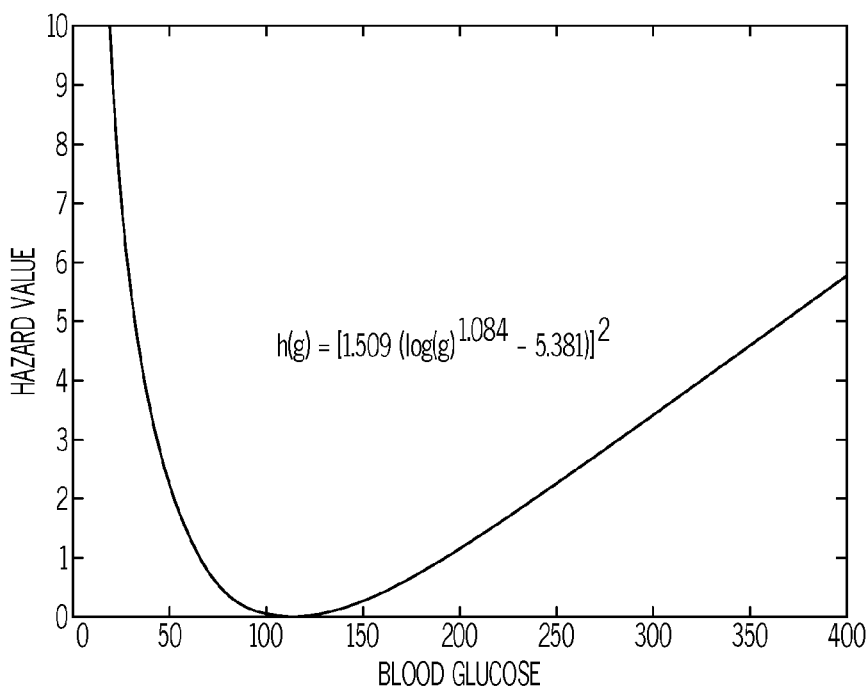
FIG. 7 is a graphical illustration of the hazard function according to the present invention.
Figure 8A:
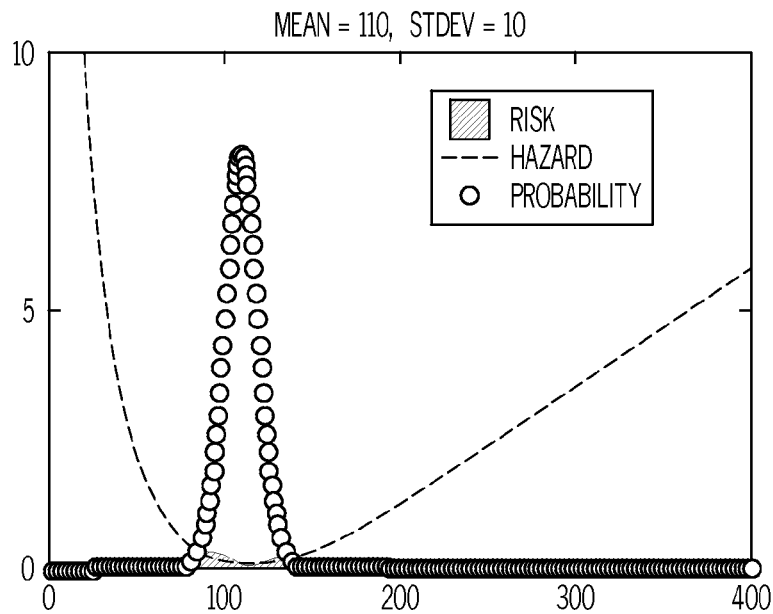
FIGS. 8A-8D are graphical views of exemplary embodiments depicting the relationship between the risk function and the hazard and probability functions according to the present invention.
Figure 8B:
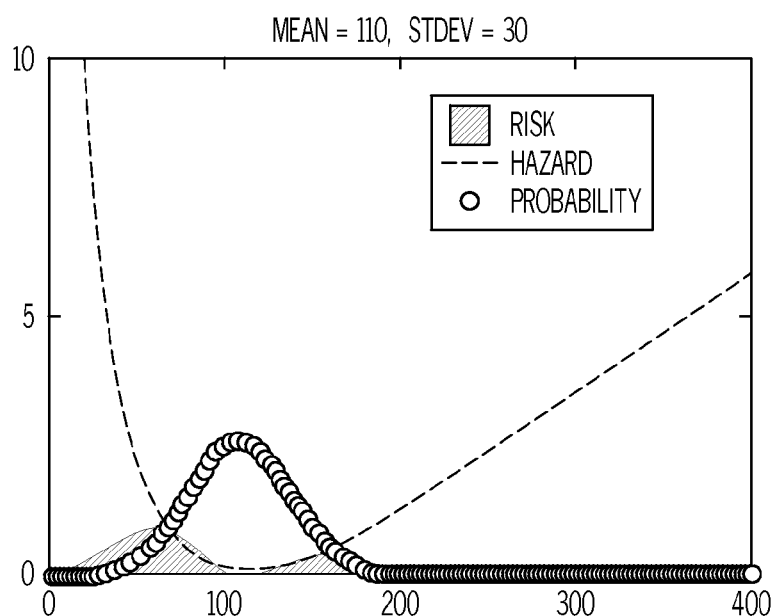
Figure 8C:
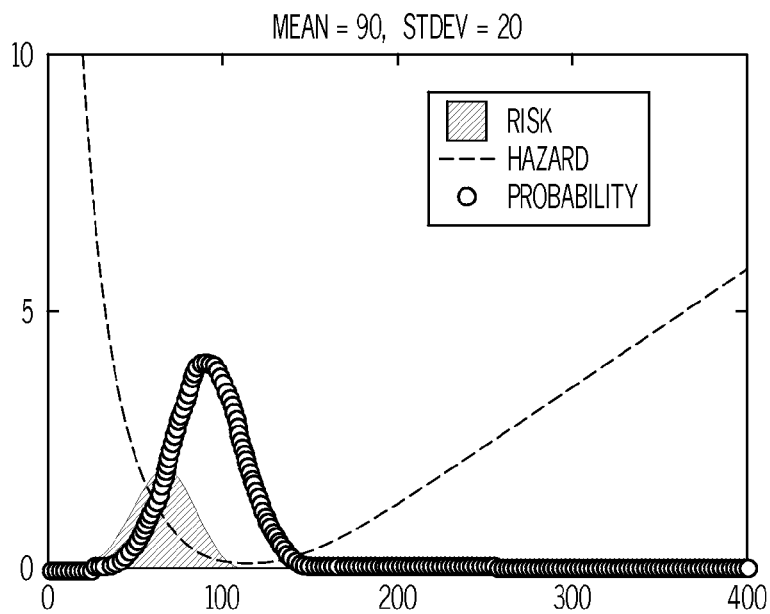
Figure 8D:
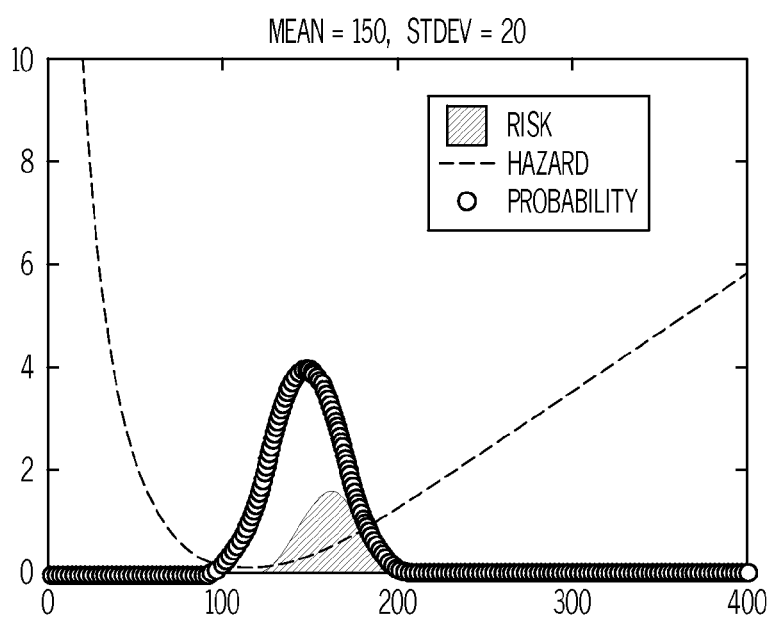

In one embodiment, the hazard function H(B) is defined by the equation $H(B)=(1.509(\log(B)^{1.0804}-5.381))^2$, wherein B is a biomarker reading in the sampling set. This is a function proposed in the following paper: Kovatchev, B. P.; Cox, D. J.; Gonder-Frederick, L. A. & Clarke, W. *Symmetrization of the blood glucose measurement scale and its applications.* Diabetes Care, 1997, 20, 1655-1658. In view of the equation and the above conceptual basis for the hazard function, it is apparent that the hazard function is asymmetric as depicted in FIG. 7.

Other functions for the hazard function are contemplated herein. For example, the hazard function H(B) may be defined by the equation $H(B)=H_{hypo}(B)+H_{hyper}(B)$, wherein B is a biomarker reading in the sampling set, $H_{hypo}(B)$ is the hazard value associated with hypoglycemic events, $H_{hyper}(B)$ is the hazard value associated with hyperglycemic events. In specific embodiments, $H_{hypo}(B)$ is $$H_{hypo}(B) = 50\left(1 - \frac{1}{1 + e - (B - 55)/5}\right) + 50e^{\frac{1}{2\cdot 30^2}B^2},$$

and $H_{hyper}(B)$ is $$H_{hyper}(B) = e^{\frac{1}{100}B}.$$

These are exemplary hazard functions, and they may be adjusted to allow the physician to select the range of biomarker readings that result in a minimal risk. This is done by adjusting the patient's therapy to achieve the minimum of the hazard function.

As graphically depicted in exemplary embodiments of FIGS. 8A-8D, the risk value for the sampling set may be obtained 580 from the risk function 570, which is the product of the probability distribution function and the hazard function as described above. The risk value is obtained from the integral of the risk function. As defined herein, the risk to a patient is the combination of the hazard associated with a biomarker reading and the probability that the patient will have that biomarker reading.

According to one embodiment, the risk value J is obtained by the following equation $$J = \int_{B=-\infty}^{\infty} p(B)H(B)dB.$$

Referring to the embodiment of FIG. 5, the optimization of insulin titration in a patient is directed to minimizing the risk value J. In accordance with the present invention, the risk value may be minimized by adjusting the diabetic patient's therapy, wherein the therapy for minimizing the risk value is selected from the group consisting of adjusting the insulin dosage 630, adjusting diabetic patient behaviors to reduce biomarker variability, adjusting a target biomarker level 640, or combinations thereof. The insulin dosage parameter may comprise a basal dosage parameter, an insulin to carbohydrate parameter, an insulin sensitivity parameter, a meal rise parameter, a meal offset parameter, an insulin active parameter, and combinations thereof. While a risk value of zero is the goal of minimization, minimizing the risk value to zero may not be attainable for all diabetic patients, thus the risk value may, in some embodiments, be considered optimized if minimized to within a tolerable proximity to zero. In one embodiment, this tolerable proximity may be set by the healthcare provider.

Referring to FIG. 5, if the risk value is minimized to an optimal level 590, then the user can exit the testing method 600. As defined herein, the risk value is considered to be minimized to an optimal risk level, when the mean of the sampling set is at or substantially close to the adjusted target biomarker level or within the adjusted biomarker target range, and the current variance or noise is within a similar noise range of the variance used to define the adjusted target biomarker level or biomarker range. In addition to risk minimization via adjustment of insulin dosage and/or the target biomarker level, the optimization methods of the present invention may also consider other patient factors, such as health, diet, and exercise, to minimize that risk value. As used herein, "substantially close" refers to a mean value that deviates from the target level by less than a specified percentage of the target value (i.e. 10%), or less than a fixed value (i.e. 10 mg/dl). Also as used herein, a "similar noise range" refers to a variance or noise that deviates from the variance or noise used to define the biomarker target level or biomarker target range of values, which typically does not require the adjustment of the target biomarker level during insulin optimization. Moreover, the noise range may be characterized as a "similar noise range" because the variance is similar or the same as the most recently calculated noise. For example, the similar noise range may equal a percentage from a previous amount of noise calculated, for example, less than a 10% change or some other fixed change amount. If the variance does not fall within the "similar noise range", it should be determined whether the variance falls within and acceptable noise range or level. Further as used herein, an "acceptable noise range" refers to a tolerable variance from the mean, which in one or more embodiments may include variance from the mean of up to about 20%, or up to about 10%, up to about 5% from the mean, or even greater variance or standard deviation from the mean. The acceptable noise range and or/the similar noise range may be estimated from the standard deviation, or it may be a value set by the healthcare provider. If the diabetic patient calculates a variance that falls outside of the similar noise range, but falls within the acceptable noise range, then the target biomarker level should be adjusted. If the variance falls outside of the acceptable noise level, the risk of a hypoglycemic event is increased, and in some embodiments, a health care provided may be notified.

Figure 10:
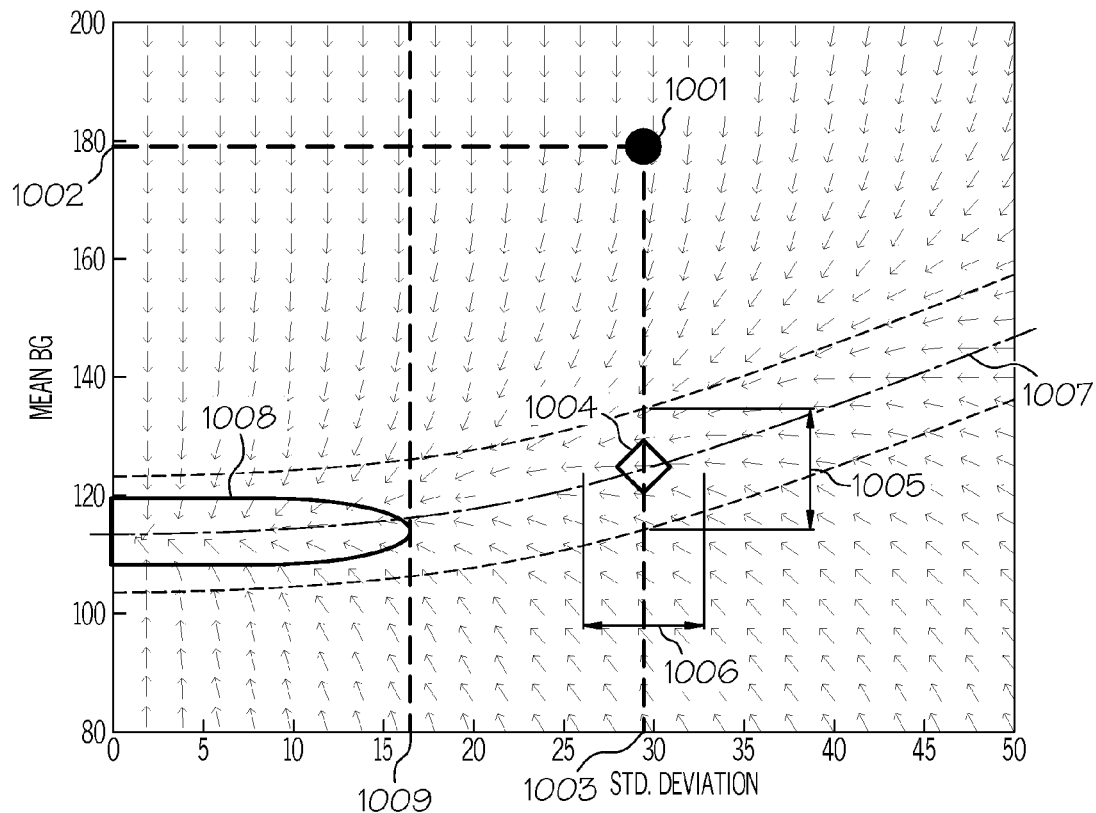
FIG. 10 illustrates a therapy gradient according to the present invention.

This may be best viewed in light of the therapy gradient embodiment of FIG. 10. As shown in FIG. 10, the calculated mean 1002 and standard deviation 1003 for the current sampling set is shown at point 1001. The target biomarker level for a given level of variance is located on the line of minimal risk 1007, and for the specific noise defined by the standard deviation 1003 is located at point 1004. The "substantially close" region 1005 to the mean and the "similar noise range" 1006 regions surround the target 1004. If the variance extends beyond the similar noise range, then a new target should be calculated. The "similar noise range" 1006 may be updated after each sampling set of biomarker data is obtained. Upon optimization, the globally optimal risk region 1008 is obtained when both the variance 1003 and mean 1002 of the biomarker sampling set are successfully optimized to within the "substantially close" region 1005 and the "similar noise range" 1006 regions surround the target 1004 and the variance 1003 is within the "acceptable noise" region 1009

If the risk value is not within optimal levels, the risk may be minimized by altering the diabetic patient's therapy. Instructions to alter a patient's therapy may be provided by a healthcare provider, or by the system itself (i.e., the electronic device e.g., blood glucose meter or a paper instruction form). If the mean is not substantially close to the target biomarker level or within the biomarker value range, but the standard deviation is within a similar noise range as the target, then the insulin dosage level must be adjusted to achieve the target biomarker level 630. If the mean is not substantially close to the target biomarker level and the standard deviation does not fall within a similar noise range, then the insulin dosage should be adjusted 630 and the biomarker target level (or setpoint) may be adjusted 640. In addition to adjusting the insulin dosage and the biomarker target level, it is also contemplated that lifestyle changes, such as exercise and diet, may also be used to minimize the risk.

In cases where the mean deviates significantly from the target and the standard deviation is significantly above the similar noise range, then the healthcare provider or the system may consider adjusting the insulin dosage or the biomarker target level or range as stated above. Additionally, the sampling set data may also lead the healthcare provider to consider a therapy change, either by adding diet and exercise, and the like, or by changing to different insulin therapies or different insulin delivery vehicles, for example, multiple daily injections of basal-bolus insulin, or insulin pumps. The sampling set data may also help the healthcare provider to identify potential life changes in the diabetic person.

The minimization of the risk value to the optimal level may also require a predetermined acceptable level of risk for hyperglycemia or hypoglycemia. For cases where the hazard penalty values raise the risk value to a non-optimal level, the one or more biomarker readings indicative of such an adverse event should be ascertained. At which point, the next optional steps may be to exit the testing method and notify a healthcare provider. Alternatively, it is contemplated that the next steps may be adjusting the insulin dosage, the target level, or both to try to eliminate the risk of an adverse event in a subsequent sampling set of biomarker data.

Figure 9:
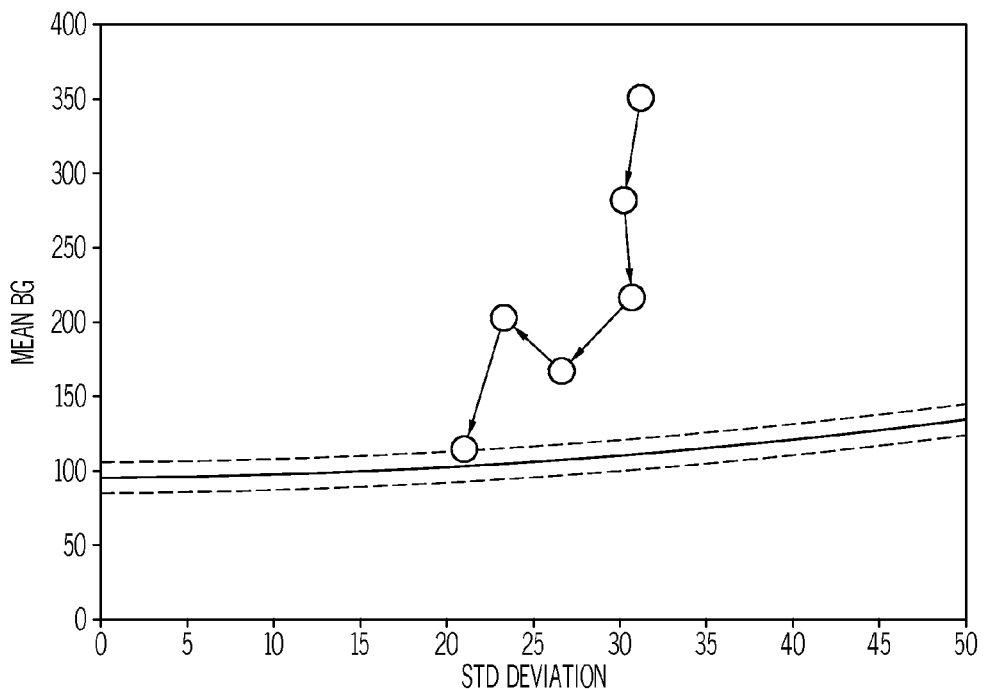
FIG. 9 shows a risk surface according to the present invention.

In addition to the quantitative mathematical illustration of risk minimization provided above, it is also possible to illustrate risk minimization through a visual illustration such as a risk surface as shown in FIG. 9. When the hazard function is calculated over a range of probability distributions defined by a mean and standard deviation, it may create a risk surface as depicted in FIG. 9. Therapy can be selected to minimize the risk, or perform gradient descent on the risk surface as shown in FIG. 10. As shown in FIGS. 9 and 10, a range of plus or minus 10 mg/dl are placed around the minimum and this range defines the target criteria for titration. Other methods for setting the target range include using ±10% of the optimal BG or as the range within a specified tolerance of the minimal risk value. In practice, fasting BG measurements (biomarker readings) from a patient would be used to determine the patient's current location on the risk surface. As the patient's therapy continues, the evolution of the patient's location on the risk surface could be plotted over time to track patient compliance and improvement. This would provide a simple visual method for quickly evaluating the progress of a patient.

As shown above, the risk surface can also be viewed by plotting the gradient direction as shown in FIG. 10. In general, titration affects the biomarker readings (mean blood glucose), thus in regions where the gradient is vertical, the best therapy would be to further adjust the insulin dosage. When the biomarker reading is optimized, the gradient points toward reducing the variability of the biomarker reading, so the physician can then change therapy strategies. The patient can be continually evaluated to determine his location on the risk surface, and then determine best therapy or advice to minimize the risk toward a more optimal location. This same optimization procedure can be followed with other therapy adjustments as well by matching the gradient descent direction to the effect of the therapy adjustment.

In addition to determining that an adjustment to the target or insulin dosage is necessary, it is also necessary to determine a specific therapy, routine, or regimen to minimize the risk to optimal levels. The insulin dosage may be adjusted according to an insulin adjustment regimen. As used herein, the "insulin adjustment regimen" refers to the number of insulin dosage adjustments required to achieve a target insulin level and the amount of each adjusted insulin dosage, wherein target insulin level is amount required to achieve the target biomarker level. Many suitable regimens are contemplated to adjust the insulin dosage.

In accordance with the insulin adjustment regimen of the present invention, the maximum insulin dosage to achieve the target biomarker level should first be calculated. The maximum insulin dosage to achieve the desired target biomarker level $D_{target}$ is calculated by the equation Error! Objects cannot be created from editing field codes., wherein m is the rate of change from a first mean of biomarker readings $\bar{B}_{k-1}$ to a subsequent second mean of biomarker readings $\bar{B}_k$ based on the adjustment of insulin from a first dosage $D_{k-1}$ to a subsequent second dosage $D_k$ as defined by the equation $$\frac{1}{m} = \frac{\bar{B}_k - \bar{B}_{k-1}}{D_k - D_{k-1}},$$

wherein $B_{target}$ is the target biomarker level, and the subscript k refers to the $k^{th}$ consecutive sampling set. Regardless of the calculations, the maximum insulin dosage to achieve the desired target biomarker level $D_{target}$ cannot exceed a maximum insulin dosage set by a healthcare provider. Also, the calculated maximum dosage to achieve a target biomarker level $D_{target}$ may be assessed by a healthcare provider in comparison to a calculated $D_{target}$ for a prior sampling set.

Next, the aggressiveness of the insulin adjustment regimen must be determined. As defined herein, an aggressive insulin adjustment regimen means that the insulin dosage will be adjusted to the maximum insulin dosage in the first adjustment. Additionally, other embodiments of the insulin adjustment regimen may utilize a more gradual adjustment approach wherein the insulin dosage is adjusted to the maximum level incrementally over at least two dosage adjustments. The adjusted insulin dosage $D_{k+1}$ after adjustment by the insulin adjustment regimen may be defined by the equation $D_{k+1}=D_k+\lambda \cdot m \cdot (B_{target}-\bar{B}_k)$ wherein $\lambda$ is a regimen tuning parameter which ranges from 0 to 1 and corresponds to an aggressiveness of the insulin adjustment regimen. For an aggressive insulin adjustment regimen, the $\lambda$ value will equal 1, such that the adjusted insulin dosage $D_{k+1}$ is the same as the maximum insulin dosage. For less aggressive insulin adjustment regimens, the $\lambda$ value will be 0.5 or less, or about 0.2 to about 0.3, such that the dosage adjustment will gradually occur over at least two insulin adjustments.

In addition to the insulin adjustment regimen, the target biomarker level may also be adjusted using a biomarker adjustment regimen. The target biomarker level is set to biomarker level associated with the minimal risk for a given noise level. In one embodiment, when noise levels are high the target mean glucose level is increased to minimize the risk of hypoglycemia.

FIGS. 11A and 11B, which are graphical simulations of the risk minimization of the present invention, include an initial biomarker target level (fasting blood glucose) of 100 mg/dl, and a 10 unit initial dose of insulin (Lantus®) administered for the first seven days. During the first seven days of the test, the mean (shown with the dotted line) was significantly higher than the target, and there was significant variance from the mean. As a result, the target was raised (see setpoint as illustrated in FIG. 11B) and the insulin dosage was raised to 15 units. From day 8-14, the insulin dosage was maintained at 15 units; however, the mean blood glucose was still above the setpoint and the variance was still high, but it slightly decreased. Consequently, the setpoint was decreased to reduce the mean biomarker and the insulin dosage was increase to 25 units total. This adjustment combination, which was maintained for the remainder of the simulation, yielded a mean substantially close to the target, and a variance within similar noise ranges.

Figure 12A:
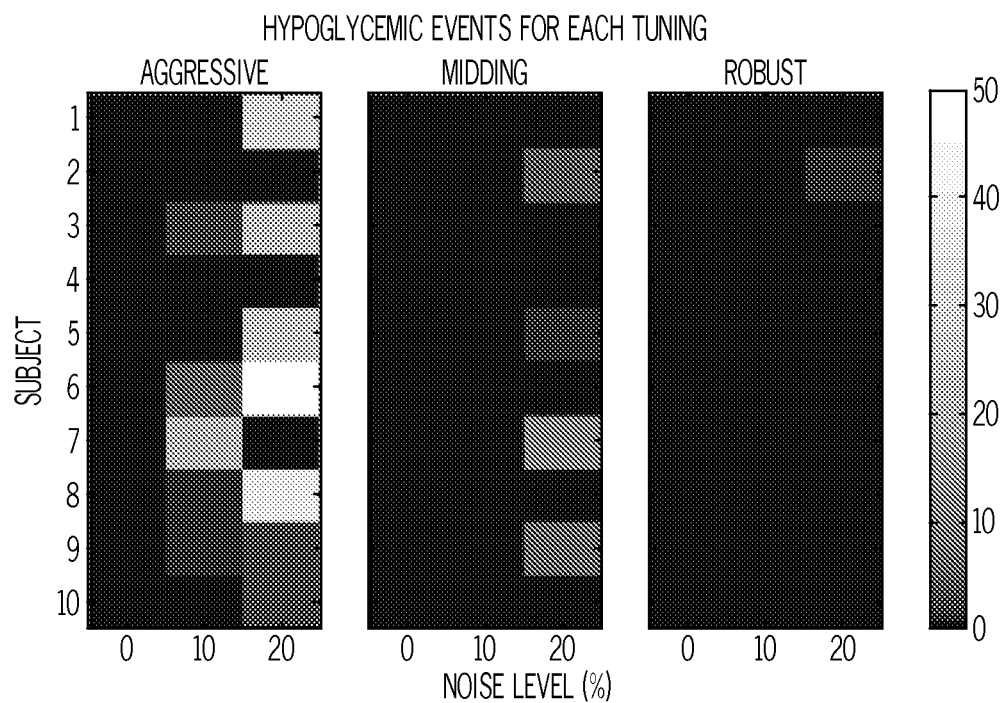
FIGS. 12A and 12B show the effect on the noise level for personalized and fixed targets when utilizing different insulin adjustment regimens according to the present invention.
Figure 12B:
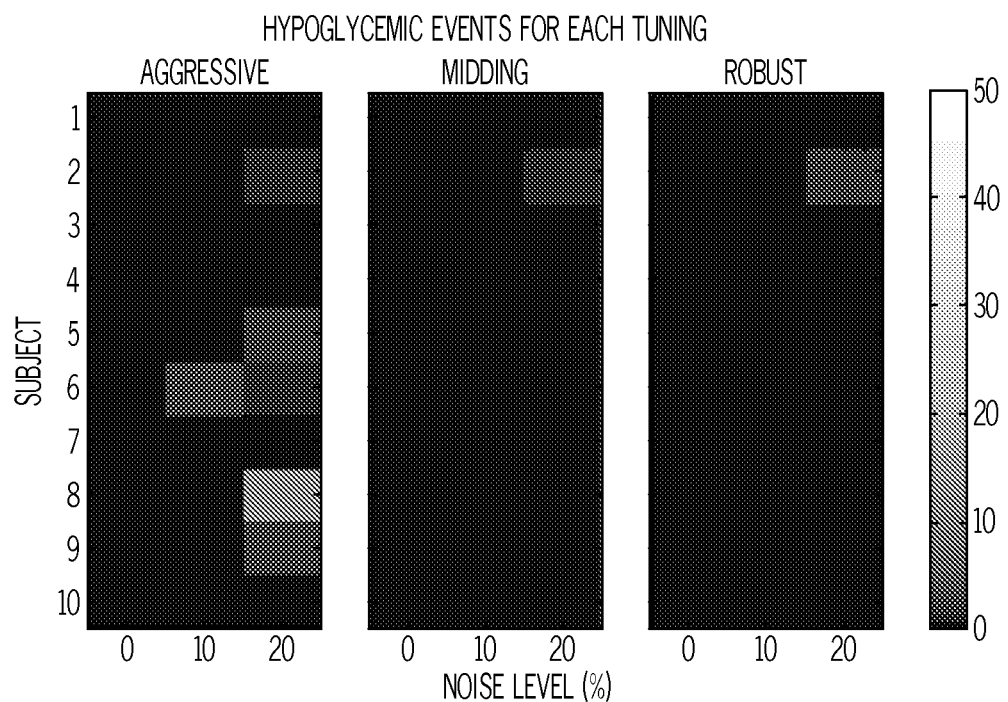

Referring to the graphical simulations of FIGS. 12A and 12B, wherein hypoglycemic events for various subjects over 100 days were studied for 10 different patients using three different adjustment regiments, robust therapy ($\lambda$=0.25), middling ($\lambda$=0.50) and aggressive therapy ($\lambda$=1), it is shown that a more gradual insulin adjustment regime has less risk of adverse events than aggressive insulin adjustment regimens using fixed target setpoints (FIG. 12A) or personalized target setpoints (FIG. 12B). Consequently, a more gradual insulin adjustment regimen may minimize hypoglycemic events in diabetic patients. Further as shown in the simulation, it was found that the risk of hypoglycemic events are minimized significantly, even at more aggressive levels of optimization, when using adjustable personalized targets in comparison to fixed biomarker target setpoints.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

All cited documents are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A testing method for optimizing a therapy to a diabetic patient via a device comprising a processor, the testing method comprising the steps of:
    querying a diabetic patient via the device to confirm that entry criteria have been satisfied;

collecting at least one sampling set of biomarker data if entry criteria have been satisfied, wherein each sampling set comprises one or more sampling instances recorded over a collection period and each sampling instance comprises one or more biomarker readings;

evaluating whether the collection of the sampling set satisfies adherence criteria;

computing a probability distribution function, a hazard function, a risk function, and a risk value for the sampling set of biomarker data wherein, the probability distribution function is calculated to approximate the probability distribution of the biomarker data, the hazard function is a function which yields higher hazard values for biomarker readings in the sampling set indicative of higher risk of complications, wherein the hazard function H(B) is defined by the equation $H(B)=H_{hypo}(B)+H_{hyper}(B)$, wherein B is a biomarker reading in the sampling set, $H_{hypo}(B)$ is the hazard function associated with hypoglycemic events, $H_{hyper}(B)$ is the hazard function associated with hyperglycemic events, the risk function is the product of the probability distribution function and the hazard function, and the risk value J is calculated by the integral of the risk function $$J = \int_{B=0}^{\infty} p(B)H(B)dB,$$

wherein p(B) is a probability distribution;

minimizing the risk value by adjusting the diabetic patient's therapy; and instructing the patient via the device to exit the testing method when the risk value for at least one sampling set is minimized to an optimal risk level, wherein the above steps are performed by the processor.

2. The testing method of claim 1 wherein the diabetic patient's therapy for minimizing the risk value is selected from the group of adjusting an insulin dosage parameter, adjusting diabetic patient behaviors to reduce biomarker variability, adjusting a target biomarker level, or combinations thereof.

3. The testing method of claim 2, wherein the insulin dosage parameter is selected from the group consisting of a basal dosage parameter, an insulin to carbohydrate parameter, an insulin sensitivity parameter, a meal rise parameter, a meal offset parameter, an insulin active parameter, and combinations thereof.

4. The testing method of claim 2 wherein the insulin dosage is variable or constant during the collection period.

5. The testing method of claim 2 wherein the insulin is basal insulin.

6. The testing method of claim 2 wherein the target biomarker level is adjusted according to a biomarker target adjustment regimen, the biomarker target adjustment regimen being defined as an adjustment or a sequence of adjustments to the target biomarker level to the level that minimizes the risk for the current amount of noise.

7. The testing method of claim 2 wherein the risk level is minimized to an optimal level when a mean of the sampling set is at a target biomarker level or adjusted target biomarker level or within a target biomarker range or an adjusted target biomarker range, and a standard deviation of the sampling set falls within a similar noise range of a prior sampling set.

8. The testing method of claim 2 further comprising adjusting the insulin dosage parameter according to an insulin adjustment regimen, which is determined by comparing the mean of the current completed sampling set to the target biomarker level, the insulin adjustment regimen being defined as the number of insulin dosage adjustments required to achieve a target insulin level and the amount of each adjusted insulin dosage, wherein the target insulin level is the amount required to achieve the target biomarker level.

9. The testing method of claim 8 wherein the insulin adjustment regimen is determined by calculating the requisite insulin dosage to achieve the target biomarker level, $D_{target}$, is calculated by the equation $D_{target}=D_k+m\cdot(B_{target}-B_k)$, wherein m is the rate of change from a first biomarker reading $B_{k-1}$ to a subsequent second biomarker reading $B_k$ based on the adjustment of insulin from a first dosage $D_{k-1}$ to a subsequent second dosage $D_k$ as defined by the equation $$\frac{1}{m} = \frac{B_k - B_{k-1}}{D_k - D_{k-1}};$$

and $B_{target}$ is the target biomarker level.

10. The testing method of claim 9 wherein the adjusted insulin dosage cannot exceed a maximum insulin dosage set by a healthcare provider.

11. The testing method of claim 9 wherein the calculated insulin dosage to achieve the target biomarker level, $D_{target}$ for the sampling set is assessed by a healthcare provider in comparison to a calculated $D_{target}$ for a prior sampling set.

12. The testing method of claim 9, wherein the calculated maximum dosage to achieve a target biomarker level $D_{target}$ is assessed against a maximum insulin dosage set by a healthcare provider.

13. The testing method of claim 9 wherein an adjusted insulin dosage $D_{k+1}$ after adjustment by the insulin adjustment regimen is calculated by the equation $D_{k+1}=Dk+\lambda\cdot m\cdot(B_{target}-B_k)$ wherein $\lambda$ is a regimen tuning parameter which ranges from 0 to 1 and corresponds to an aggressiveness of the insulin adjustment regimen.

14. The testing method of claim 13 wherein an aggressive insulin adjustment regimen adjusts an insulin dosage to the maximum level in a first adjustment, and includes a $\lambda$ value of 1.

15. The testing method of claim 13 wherein a less aggressive insulin adjustment regimen adjusts an insulin dosage to the maximum level incrementally over at least two dosage adjustments, and includes a $\lambda$ value of 0.5 or less.

16. The testing method of claim 1 wherein the optimal risk level may be set by a physician.

17. The testing method of claim 1 wherein the probability distribution function is calculated from a mean and standard deviation of the sampling set.

18. The testing method of claim 1 wherein the probability distribution function is calculated using a kernel density estimator.

19. The testing method of claim 1 wherein the hazard function is a function which yields higher hazard values for biomarker readings in the sampling set indicative of hyperglycemia or hypoglycemia and yields hazard values at or near zero at a target biomarker level or within a target biomarker range.

20. The testing method of claim 1 wherein for minimization of the risk value to the optimal level, there are no hazard values indicative of a hyperglycemic or hypoglycemic event.

21. The testing method of claim 1 wherein the collection period for the sampling set is defined as multiple sampling instances within a day, multiple sampling instances within a week, multiple sampling instances within consecutive weeks, or multiple sampling instances on consecutive days within a week.

22. The testing method of claim 1 wherein each sampling instance comprises the biomarker reading and other contextual data associated with the biomarker reading, wherein the contextual data is selected from the group consisting of the time of collection, the date of collection, the time when the last meal was consumed, stress, exercise, energy level, the time and dose of medications including insulin, the recommended amount of insulin, and combinations thereof.

23. The testing method of claim 1 wherein the biomarker readings are fasting blood glucose readings.

24. The testing method of claim 1 wherein the biomarker reading includes information concerning a biomarker type selected from glucose, triglycerides, low density lipids, and high density lipids.

25. The testing method of claim 1 wherein the hazard function H(B) is defined by the equation $H(B)=(1.509(\log(B)^{1.0804}-5.381))^2$, wherein B is a biomarker reading in the sampling set.

26. The testing method of claim 1 wherein the hazard function is an index which correlates a biomarker reading to a corresponding hazard value.

27. The testing method of claim 1 further comprising collecting one or more additional sampling sets of biomarker data when the risk level is not at an optimal level.

28. The testing method of claim 1 further comprising conducting a new testing plan after the risk is minimized to an optimal level.

29. The testing method of claim 1 wherein the adherence criteria requires a fasting period before collection of the sampling set of biomarker data.

30. The testing method of claim 1 further comprising determining whether to adjust a target biomarker level based on a variance of the sampling set, wherein
   a variance within a similar noise range does not require the adjustment of the target biomarker level, the similar noise range being the variance computed from one or more prior sampling sets; and
   a variance within an acceptable noise range requires adjustment of the target biomarker level, the acceptable noise range being a maximum tolerable variance for a sampling set.

31. The testing method of claim 30 wherein the similar noise range is less than a 10% change from a previous amount of noise calculated.

32. The testing method of claim 30 further comprising contacting a physician when the variance is greater than the acceptable noise range.

33. A device configured to guide a diabetic patient through a testing plan directed to optimizing an administration dosage of insulin, comprising:
   a processor coupled to memory, wherein the memory comprises collection procedures; and
   software having instructions that when executed by the processor causes the processor to:
      determine whether entry criteria for the diabetic patient to begin the testing plan have been met;
      instruct the diabetic patient to collect one or more sampling sets of biomarker data in accordance with the collection procedures, wherein each sampling set comprises one or more sampling instances recorded over a collection period, and each sampling instance comprises one or more biomarker readings;
      evaluate whether the collection of the sampling set satisfies adherence criteria; and
      compute a probability distribution function, a hazard function, a risk function, and a risk value for the sampling set of biomarker data wherein,
         the probability distribution function is calculated to approximate the probability distribution of the biomarker data,
         the hazard function is a function which yields higher hazard values for biomarker readings in the sampling set indicative of higher risk of complications, wherein the hazard function H(B) is defined by the equation $H(B)=H_{hypo}(B)+H_{hyper}(B)$, wherein B is a biomarker reading in the sampling set, $H_{hypo}(B)$ is the hazard function associated with hypoglycemic events, $H_{hyper}(B)$ is the hazard function associated with hyperglycemic events,
         the risk function is the product of the probability distribution function and the hazard function, and
         the risk value J is calculated by the integral of the risk function $$J = \int_{B=0}^{\infty} p(B)H(B)dB,$$

wherein p(B) is a probability distribution;
      instruct the diabetic patient to minimize the risk value by adjusting the patient's therapy, or exit the testing method if the risk value for at least one sampling set is minimized to an optimal risk level.

34. The device of claim 33 wherein the diabetic patient's therapy for minimizing the risk value is selected from the group consisting of adjusting the insulin dosage, adjusting diabetic patient behaviors to reduce biomarker variability, adjusting a target biomarker level, or combinations thereof.

35. The device of claim 33 wherein, for minimization of the risk value to the optimal level, there are no hazard values indicative of a hyperglycemic or hypoglycemic event.

36. The device of claim 33 wherein the collection device is a continuous glucose monitor to obtain time-resolved glucose information that is provided as biomarker data to the processor.

37. The device of claim 33 further comprising a therapy device configured to administer insulin to a diabetic patient.

38. The device of claim 33 wherein the therapy device is an insulin pen.

39. The device of claim 33 further comprising a lancet operable to pierce the skin of the diabetic patient to obtain a blood glucose biomarker.

40. The device of claim 33 further comprising a meter configured to measure one or more selected biomarkers.

41. The device of claim 30 wherein the software instructions when executed causes the processor to determine whether to adjust a target biomarker level based on a variance of the sampling set, wherein
   a variance within a similar noise range does not require the adjustment of the target biomarker level, the similar noise range being the variance computed from one or more prior sampling sets; and a variance within an acceptable noise range requires adjustment of the target biomarker level, the acceptable noise range being the maximum tolerable variance for a sampling set.

42. The testing method of claim 41 wherein a physician is contacted when the variance is greater than the acceptable noise range.

43. A testing method for optimizing a therapy to a diabetic patient via a device comprising a processor, the testing method comprising the steps of:
querying a diabetic patient via the device to confirm that entry criteria have been satisfied;
collecting at least one sampling set of biomarker data if entry criteria have been satisfied, wherein each sampling set comprises one or more sampling instances recorded over a collection period and each sampling instance comprises one or more biomarker readings;
evaluating whether the collection of the sampling set satisfies adherence criteria;
computing a probability distribution function, a hazard function, a risk function, and a risk value for the sampling set of biomarker data wherein,
the probability distribution function is calculated to approximate the probability distribution of the biomarker data,
the hazard function is a function which yields higher hazard values for biomarker readings in the sampling set indicative of higher risk of complications, wherein the hazard function H(B) is defined by the equation H(B) =$H_{hypo}$(B)+$H_{hyper}$(B), wherein B is a biomarker reading in the sampling set, $H_{hypo}$(B) is the hazard function associated with hypoglycemic events, $H_{hyper}$(B) is the hazard function associated with hyperglycemic events, wherein $$H_{hypo}(B) = 50\left(1 - \frac{1}{1 + e - (B - 55)/5}\right) + 50e^{\frac{1}{2\cdot 30^2}B^2}, \text{ and}$$

$$H_{hyper}(B) \text{ is } H_{hyper}(B) = e^{\frac{1}{100}B},$$

the risk function is the product of the probability distribution function and the hazard function, and
the risk value is calculated by the integral of the risk function minimizing the risk value by adjusting the diabetic patient's therapy; and
instructing the patient via the device to exit the testing method when the risk value for at least one sampling set is minimized to an optimal risk level,
wherein the above steps are performed by the processor.

44. The testing method of claim 43 wherein each sampling instance comprises the biomarker reading and other contextual data associated with the biomarker reading, wherein the contextual data is selected from the group consisting of the time of collection, the date of collection, the time when the last meal was consumed, stress, exercise, energy level, the time and dose of medications including insulin, the recommended amount of insulin, and combinations thereof.

45. The testing method of claim 43 further comprising determining whether to adjust a target biomarker level based on a variance of the sampling set, wherein
a variance within a similar noise range does not require the adjustment of the target biomarker level, the similar noise range being the variance computed from one or more prior sampling sets; and
a variance within an acceptable noise range requires adjustment of the target biomarker level, the acceptable noise range being a maximum tolerable variance for a sampling set.

46. The testing method of claim 45 further comprising contacting a physician when the variance is greater than the acceptable noise range.

47. The testing method of claim 43 wherein the diabetic patient's therapy for minimizing the risk value is selected from the group of adjusting an insulin dosage parameter, adjusting diabetic patient behaviors to reduce biomarker variability, adjusting a target biomarker level, or combinations thereof.

48. The testing method of claim 47, wherein the insulin dosage parameter is selected from the group consisting of a basal dosage parameter, an insulin to carbohydrate parameter, an insulin sensitivity parameter, a meal rise parameter, a meal offset parameter, an insulin active parameter, and combinations thereof.

49. The testing method of claim 47 wherein for minimization of the risk value to the optimal level, there are no hazard values indicative of a hyperglycemic or hypoglycemic event.

50. The testing method of claim 47 further comprising adjusting the insulin dosage parameter according to an insulin adjustment regimen, which is determined by comparing the mean of the current completed sampling set to the target biomarker level, the insulin adjustment regimen being defined as the number of insulin dosage adjustments required to achieve a target insulin level and the amount of each adjusted insulin dosage, wherein the target insulin level is the amount required to achieve the target biomarker level.

51. The testing method of claim 50 wherein the insulin adjustment regimen is determined by calculating the requisite insulin dosage to achieve the target biomarker level, $D_{target}$, is calculated by the equation $D_{target}=D_k+m\cdot(B_{target}-B_k)$, wherein
m is the rate of change from a first biomarker reading $B_{k-1}$ to a subsequent second biomarker reading $B_k$ based on the adjustment of insulin from a first dosage $D_{k-1}$ to a subsequent second dosage $D_k$ as defined by the equation $$\frac{1}{m} = \frac{B_k - B_{k-1}}{D_k - D_{k-1}};$$

and
$B_{target}$ is the target biomarker level.

52. The testing method of claim 51 wherein an adjusted insulin dosage $D_{k+1}$ after adjustment by the insulin adjustment regimen is calculated by the equation $D_{k+1}=Dk+\lambda\cdot m\cdot(B_{target}-B_k)$ wherein $\lambda$ is a regimen tuning parameter which ranges from 0 to 1 and corresponds to an aggressiveness of the insulin adjustment regimen.

53. The testing method of claim 52 wherein an aggressive insulin adjustment regimen adjusts an insulin dosage to the maximum level in a first adjustment, and includes a $\lambda$ value of 1.

54. The testing method of claim 52 wherein a less aggressive insulin adjustment regimen adjusts an insulin dosage to the maximum level incrementally over at least two dosage adjustments, and includes a $\lambda$ value of 0.5 or less.

55. The testing method of claim 52 wherein the adjusted insulin dosage cannot exceed a maximum insulin dosage set by a healthcare provider.

56. The testing method of claim 52 wherein the calculated insulin dosage to achieve the target biomarker level, $D_{target}$ for the sampling set is assessed by a healthcare provider in comparison to a calculated $D_{target}$ for a prior sampling set.

57. A testing method for optimizing a therapy to a diabetic patient via a device comprising a processor, the testing method comprising the steps of:
   querying a diabetic patient via the device to confirm that entry criteria have been satisfied;
   collecting at least one sampling set of biomarker data if entry criteria have been satisfied, wherein each sampling set comprises one or more sampling instances recorded over a collection period and each sampling instance comprises one or more biomarker readings;
   evaluating whether the collection of the sampling set satisfies adherence criteria;
   computing a probability distribution function, a hazard function, a risk function, and a risk value for the sampling set of biomarker data wherein,
      the probability distribution function is calculated to approximate the probability distribution of the biomarker data,
      the hazard function is a function which yields higher hazard values for biomarker readings in the sampling set indicative of higher risk of complications,
      the risk function is the product of the probability distribution function and the hazard function, and
      the risk value is calculated by the integral of the risk function,
   minimizing the risk value by adjusting the diabetic patient's insulin dosage according to an insulin adjustment regimen, which is determined by comparing the mean of the current completed sampling set to the target biomarker level, the insulin adjustment regimen being defined as the number of insulin dosage adjustments required to achieve a target insulin level and the amount of each adjusted insulin dosage, wherein the target insulin level is the amount required to achieve the target biomarker level, wherein the insulin adjustment regimen is determined by calculating the requisite insulin dosage to achieve the target biomarker level, $D_{target}$, is calculated by the equation $D_{target}=D_k+m\cdot(B_{target}-B_k)$, wherein m is the rate of change from a first biomarker reading $B_{k-1}$ to a subsequent second biomarker reading $B_k$ based on the adjustment of insulin from a first dosage $D_{k-1}$ to a subsequent second dosage $D_k$ as defined by the equation $$\frac{1}{m} = \frac{B_k - B_{k-1}}{D_k - D_{k-1}},$$

and $B_{target}$ is the target biomarker level, wherein an adjusted insulin dosage $D_{k+1}$ after adjustment by the insulin adjustment regimen is calculated by the equation $D_{k+1}=Dk+\lambda\cdot m\cdot(B_{target}-B_k)$ wherein $\lambda$ is a regimen tuning parameter which ranges from 0 to 1 and corresponds to an aggressiveness of the insulin adjustment regimen; and
   instructing the patient via the device to exit the testing method when the risk value for at least one sampling set is minimized to an optimal risk level,
   wherein the above steps are performed by the processor.

58. The testing method of claim 57 wherein an aggressive insulin adjustment regimen adjusts an insulin dosage to the maximum level in a first adjustment, and includes a $\lambda$ value of 1.

59. The testing method of claim 57 wherein a less aggressive insulin adjustment regimen adjusts an insulin dosage to the maximum level incrementally over at least two dosage adjustments, and includes a $\lambda$ value of 0.5 or less.

60. The testing method of claim 57 wherein the adjusted insulin dosage cannot exceed a maximum insulin dosage set by a healthcare provider.

61. The testing method of claim 57 wherein the calculated insulin dosage to achieve the target biomarker level, $D_{target}$ for the sampling set is assessed by a healthcare provider in comparison to a calculated $D_{target}$ for a prior sampling set.

* * * * *

UNITED STATES PATENT AND TRADEMARK OFFICE
CERTIFICATE OF CORRECTION

PATENT NO. : 8,532,933 B2
APPLICATION NO. : 12/818795
DATED : September 10, 2013
INVENTOR(S) : David L. Duke et al.

It is certified that error appears in the above-identified patent and that said Letters Patent is hereby corrected as shown below:

Title Page

Item (57)   "ABSTRACT
Embodiments of a testing method for optimizing a therapy to a diabetic patient comprise collecting at least one sampling set of biomarker data, computing a probability distribution function, a hazard function, a risk function, and a risk value for the sampling set of biomarker data wherein, wherein the probability distribution function is calculated to approximate the probability distribution of the biomarker data, the hazard function is a function which yields higher hazard values for biomarker readings in the sampling set indicative of higher risk of complications, the risk function is the product of the probability distribution function and the hazard function, and the risk value is calculated by the integral of the risk function, minimizing the risk value by adjusting the diabetic patient's therapy, and exiting the testing method when the risk value for at least one sampling set is minimized to an optimal risk level."

should read:

(57)   --ABSTRACT
Embodiments of a testing method for optimizing a therapy to a diabetic patient comprise collecting at least one sampling set of biomarker data, computing a probability distribution function, a hazard function, a risk function, and a risk value for the sampling set of biomarker data, wherein the probability distribution function is calculated to approximate the probability distribution of the biomarker data, the hazard function is a function which yields higher hazard values for biomarker readings in the sampling set indicative of higher risk of complications, the risk function is the product of the probability distribution function and the hazard function, and the risk value is calculated by the integral of the risk function, minimizing the risk value by adjusting the diabetic patient's therapy, and exiting the testing method when the risk value for at least one sampling set is minimized to an optimal risk level.--

Signed and Sealed this
First Day of July, 2014

Michelle K. Lee
*Deputy Director of the United States Patent and Trademark Office*

CERTIFICATE OF CORRECTION (continued)
U.S. Pat. No. 8,532,933 B2

In the Claims

Col. 24, Claim 13, Lines 41-42, "$D_{k+1} = Dk + \lambda \cdot m \cdot (B_{target} - B_k)$" should read -- $D_{k+1} = D_k + \lambda \cdot m \cdot (B_{target} - B_k)$ --;

Col. 28, Claim 52, Lines 51-52, "$D_{k+1} = Dk + \lambda \cdot m \cdot (B_{target} - B_k)$" should read -- $D_{k+1} = D_k + \lambda \cdot m \cdot (B_{target} - B_k)$ --; and Col. 30, Claim 57, Lines 15-16, "$D_{k+1} = Dk + \lambda \cdot m \cdot (B_{target} - B_k)$" should read -- $D_{k+1} = D_k + \lambda \cdot m \cdot (B_{target} - B_k)$ --.